US011241367B2

(12) United States Patent
Sharaiha

(10) Patent No.: US 11,241,367 B2
(45) Date of Patent: Feb. 8, 2022

(54) NASOGASTRIC TUBE HOLDING ASSEMBLIES

(71) Applicant: ASPISAFE SOLUTIONS INC., New York, NY (US)

(72) Inventor: Talal Sharaiha, New York, NY (US)

(*) Notice: Subject to any disclaimer, the term of this patent is extended or adjusted under 35 U.S.C. 154(b) by 302 days.

(21) Appl. No.: 16/451,544

(22) Filed: Jun. 25, 2019

(65) Prior Publication Data

US 2019/0388303 A1 Dec. 26, 2019

Related U.S. Application Data

(60) Provisional application No. 62/689,386, filed on Jun. 25, 2018.

(51) Int. Cl.
*A61J 15/00* (2006.01)
*A61M 25/02* (2006.01)

(52) U.S. Cl.
CPC ....... *A61J 15/0061* (2013.01); *A61J 15/0003* (2013.01); *A61M 2025/0206* (2013.01); *A61M 2025/0226* (2013.01)

(58) Field of Classification Search
CPC .. A61M 2025/0206; A61M 2025/0213; A61M 2025/022; A61M 2025/0226; A61M 2025/0253; A61M 2025/026; A61M 25/02; A61J 15/0061; A61J 15/0057; A61J 15/0053
See application file for complete search history.

(56) References Cited

U.S. PATENT DOCUMENTS

| | | | | |
|---|---|---|---|---|
| 3,055,371 A * | 9/1962 | Kulick | ................. | A61M 25/02 606/192 |
| 4,373,523 A * | 2/1983 | Treutelaar | .............. | A61B 17/12 128/207.18 |
| 4,480,639 A | 11/1984 | Peterson et al. | | |
| 4,744,358 A * | 5/1988 | McGinnis | ......... | A61M 16/0488 128/207.17 |
| 5,345,931 A * | 9/1994 | Battaglia, Jr. | ...... | A61M 16/0488 128/207.17 |
| 5,382,239 A * | 1/1995 | Orr | ........................ | A61M 25/02 604/177 |
| 5,438,979 A | 8/1995 | Johnson, Jr. et al. | | |
| 5,490,504 A * | 2/1996 | Vrona | ................ | A61M 16/0488 128/207.14 |
| 6,067,985 A * | 5/2000 | Islava | ................ | A61M 16/0488 128/207.17 |
| 2012/0168571 A1* | 7/2012 | Bond | ................. | A61M 16/0488 248/70 |
| 2012/0227747 A1* | 9/2012 | Levine | .............. | A61M 16/0493 128/207.14 |
| 2014/0261462 A1* | 9/2014 | Visconti | ................. | A61M 25/02 128/861 |
| 2014/0261463 A1* | 9/2014 | Visconti | ............. | A61M 16/0497 128/861 |
| 2016/0030696 A1 | 2/2016 | Klenner et al. | | |
| 2017/0197049 A1* | 7/2017 | Doll | ..................... | A61J 15/0053 |

* cited by examiner

*Primary Examiner* — Nilay J Shah
(74) *Attorney, Agent, or Firm* — Van Court & Aldridge LLP

(57) ABSTRACT

Tube holding assemblies and methods for using and making the same are provided, including an assembly for holding a nasogastric tube to a patient's head while also being adjustable along a track that may be positioned underneath the patient's nose but above the patient's mouth and about an axis of rotation.

20 Claims, 20 Drawing Sheets

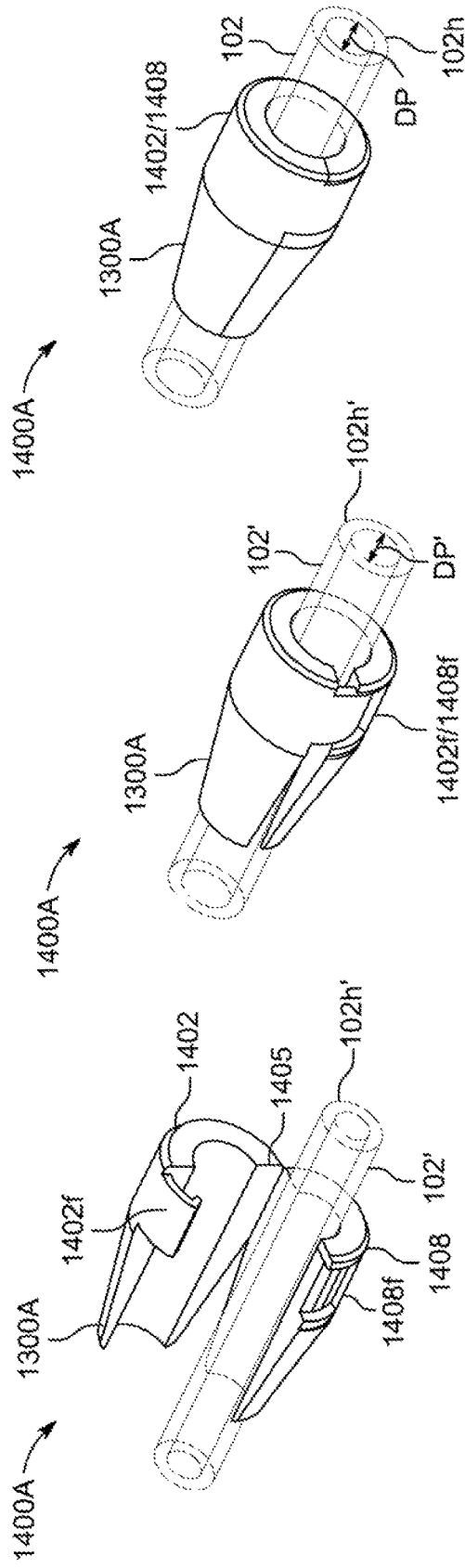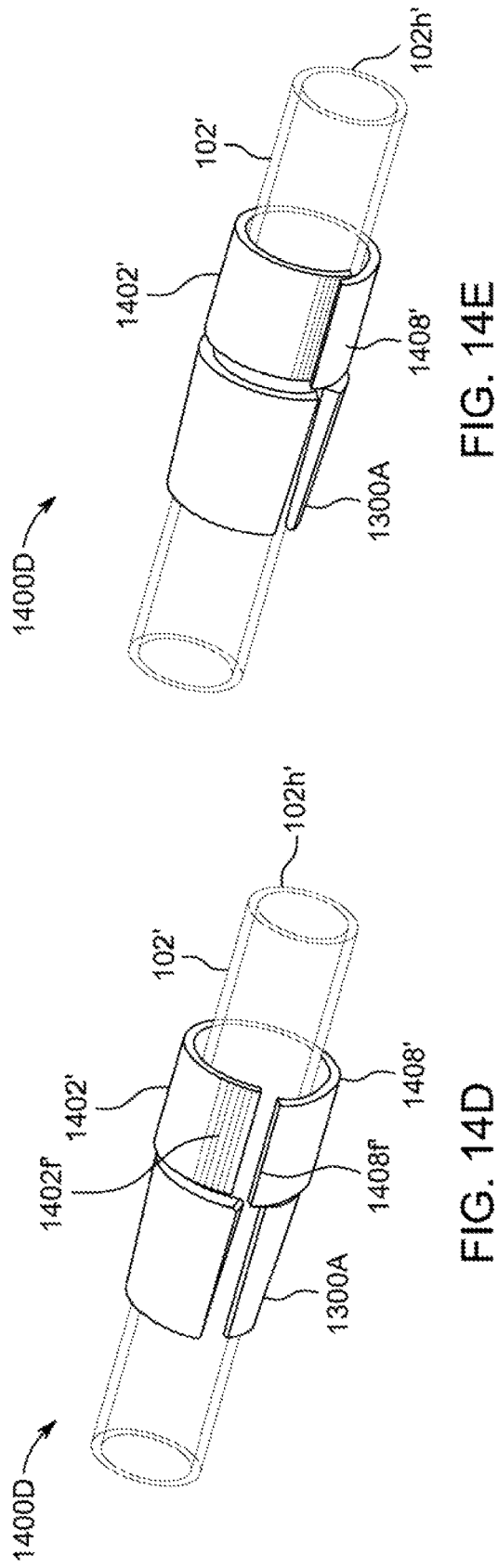

NASOGASTRIC TUBE HOLDING ASSEMBLIES

CROSS-REFERENCE TO RELATED APPLICATION(S)

This application claims the benefit of prior filed U.S. Provisional Patent Application No. 62/689,386, filed Jun. 25, 2018, which is hereby incorporated by reference herein in its entirety.

TECHNICAL FIELD

This disclosure relates to tube holding assemblies and, more particularly, to nasogastric tube holding assemblies and methods for using and making the same.

BACKGROUND OF THE DISCLOSURE

Various medical procedures (e.g., feeding and/or intubation procedures) involve a distal end of a tube being inserted into a specific area of a patient and then using the tube for injecting material into the patient and/or for removing material from the patient. However, safely securing such a tube at a particular position with respect to the patient during use has heretofore been difficult.

SUMMARY OF THE DISCLOSURE

This document describes tube holding assemblies and methods for using and making the same.

For example, an assembly for holding a nasogastric tube to a patient's head is provided that may include a mount subassembly including a base and a track extending from and along a front face of the base, a lock subassembly including a slider clamp body operative to be coupled to and slidable along the track, a tube clamp body operative to receive and hold a portion of the nasogastric tube in place with respect to the tube clamp body, and a hinge operative to allow limited movement of the slider clamp body with respect to the tube clamp body, and a strap subassembly operative to secure the mount subassembly to the patient's head.

As another example, an assembly for holding a nasogastric tube to a patient's head is provided that may include a mount subassembly defining a track, a lock subassembly including a slider clamp body operative to be coupled to and slidable along the track, a tube clamp body operative to receive and hold a portion of the nasogastric tube in place with respect to the tube clamp body, and a hinge operative to allow limited rotation of the slider clamp body with respect to the tube clamp body, and a fastener subassembly operative to secure the mount subassembly to the patient's head.

As yet another example, a method of using an assembly for holding a nasogastric tube to a patient's head once a distal end of the nasogastric tube has been functionally positioned within the patient via a nostril of a nose of the patient is provided that may include positioning a mount subassembly of the assembly underneath the nose, sliding a slider clamp body of a lock subassembly of the assembly along a track of the positioned mount subassembly until a tube clamp body of the lock subassembly is aligned with a portion of the nasogastric tube, rotating the tube clamp body with respect to the slid slider clamp body until a passageway of the tube clamp body is aligned with the portion of the nasogastric tube, and placing the portion of the nasogastric tube within the passageway of the rotated tube clamp body.

This Summary is provided only to summarize some example embodiments, so as to provide a basic understanding of some aspects of the subject matter described in this document. Accordingly, it will be appreciated that the features described in this Summary are only examples and should not be construed to narrow the scope or spirit of the subject matter described herein in any way. Unless otherwise stated, features described in the context of one example may be combined or used with features described in the context of one or more other examples. Other features, aspects, and advantages of the subject matter described herein will become apparent from the following Detailed Description, Figures, and Claims.

BRIEF DESCRIPTION OF THE DRAWINGS

The discussion below makes reference to the following drawings, in which like reference characters may refer to like parts throughout, and in which:

FIG. 14A is a front, right, top perspective view of yet another tube stopper with a locking mechanism in an open configuration about a first tube;

FIG. 14B is a front, right, top perspective view of the tube stopper with locking mechanism of FIG. 14A in a closed configuration about the first tube;

FIG. 14C is a front, right, top perspective view of the tube stopper with locking mechanism of FIGS. 14A and 14B in a closed configuration about a second tube;

FIG. 14D is a front, right, top perspective view of yet another tube stopper with a locking mechanism in an open configuration about a tube;

FIG. 14E is a front, right, top perspective view of the tube stopper with locking mechanism of FIG. 14D in a closed configuration about the tube;

DETAILED DESCRIPTION OF THE DISCLOSURE

Figure 1:
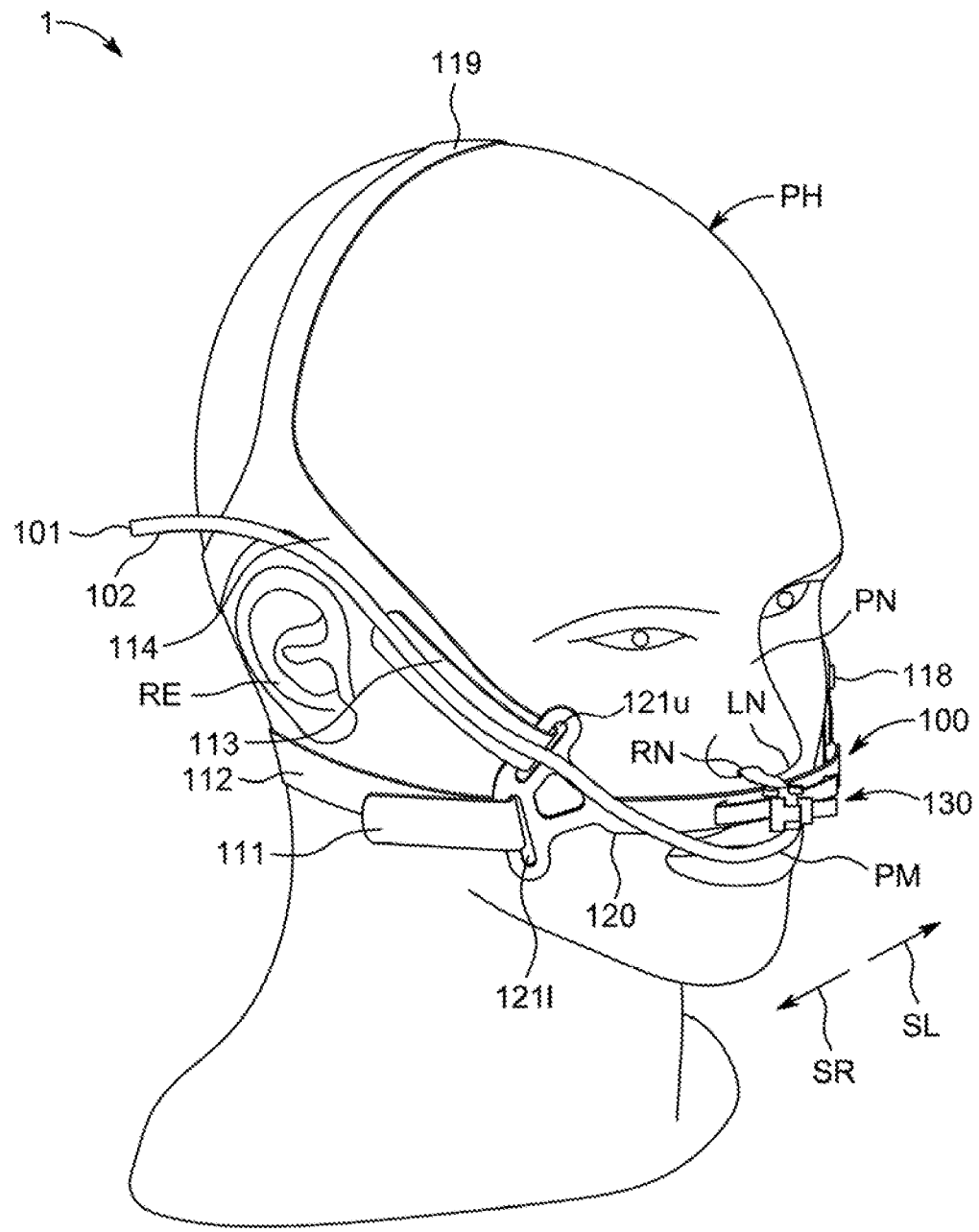
FIG. 1 is a front, right, top perspective view of a system including a patient wearing a tube holding assembly.
Figure 2:
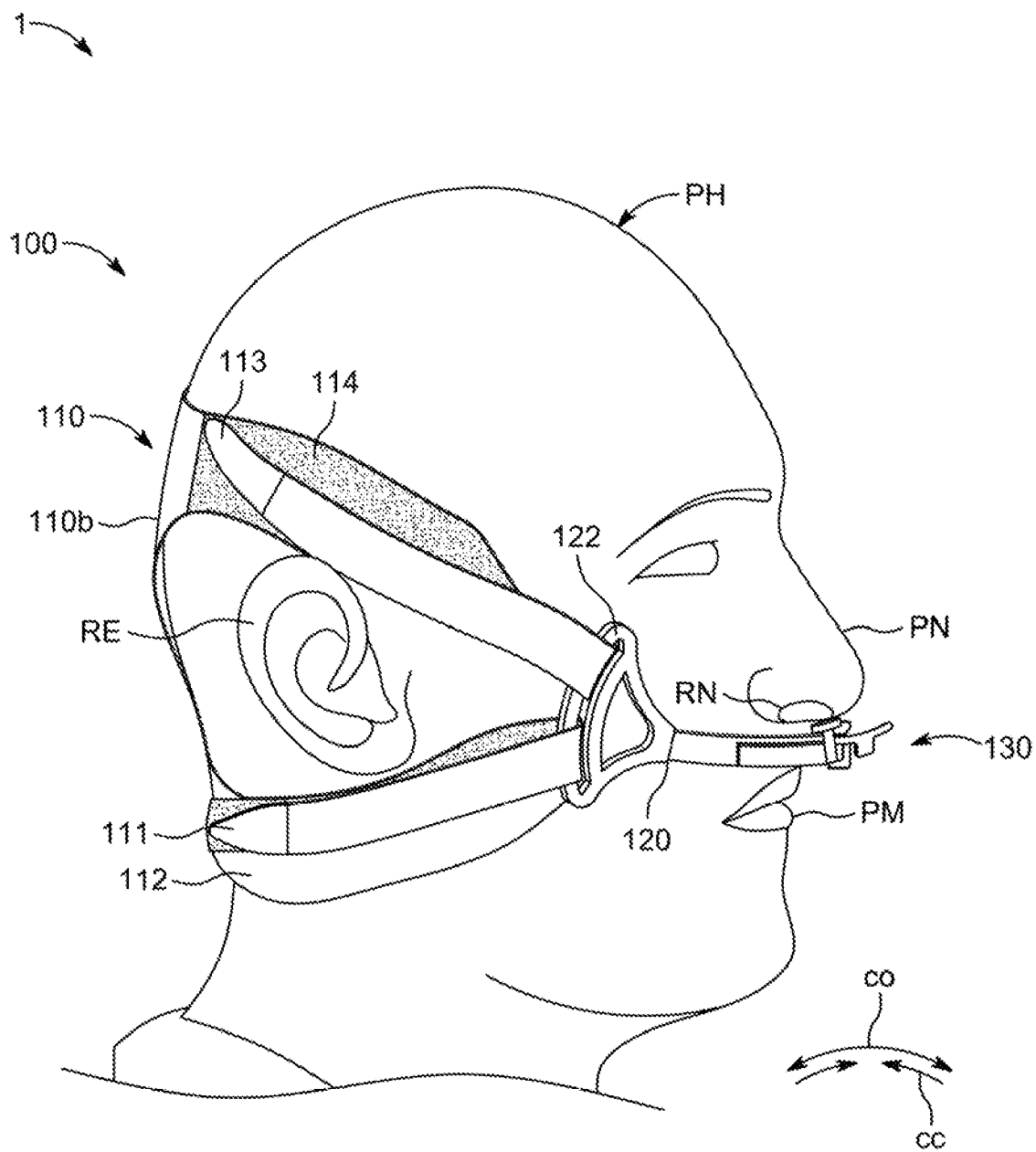
FIG. 2 is a right side view of the patient of FIG. 1 wearing a portion of the tube holding assembly of FIG. 1.
Figure 3:
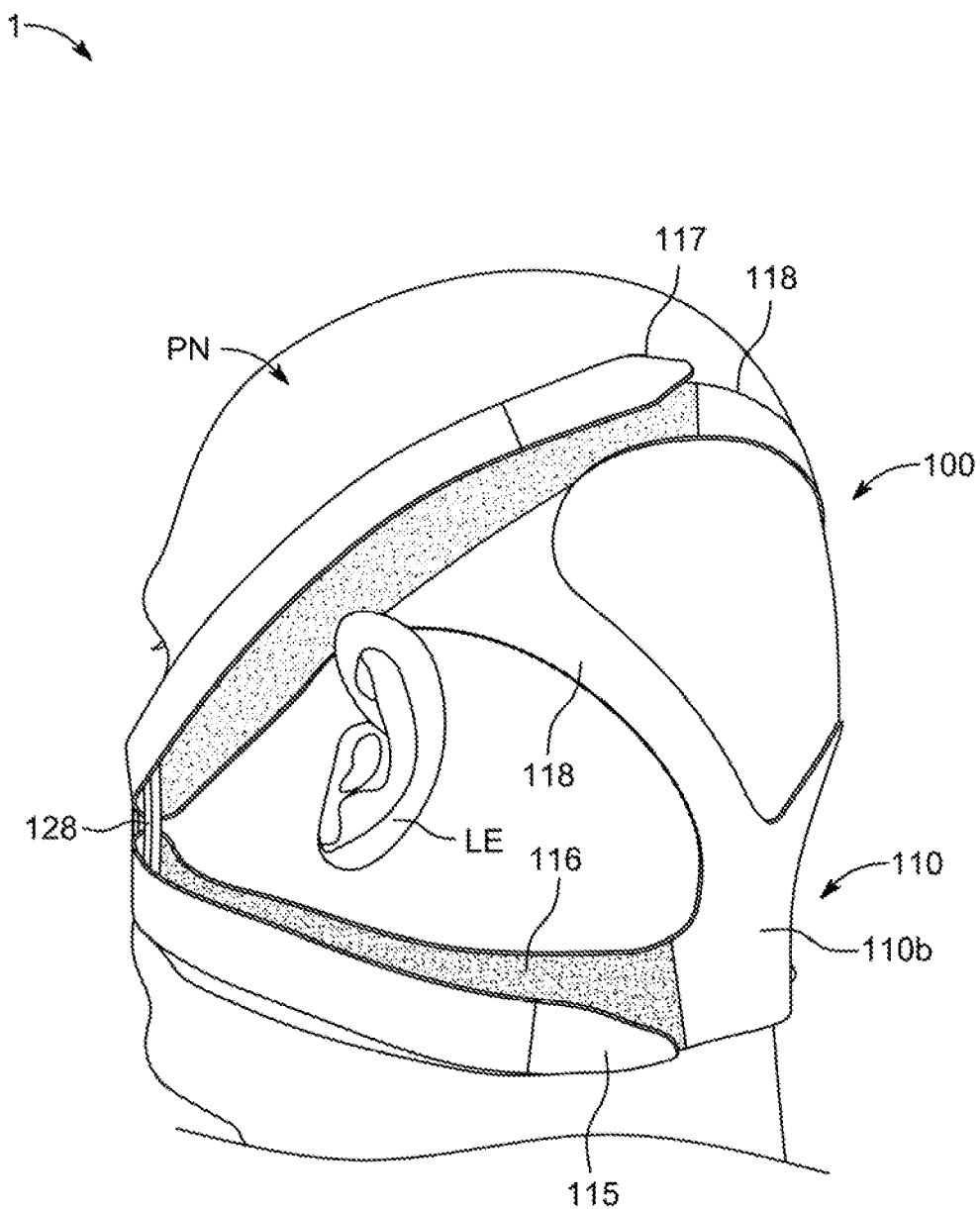
FIG. 3 is a rear, left perspective view of the patient of FIGS. 1 and 2 wearing the tube holding assembly of FIGS. 1 and 2.
Figure 7:
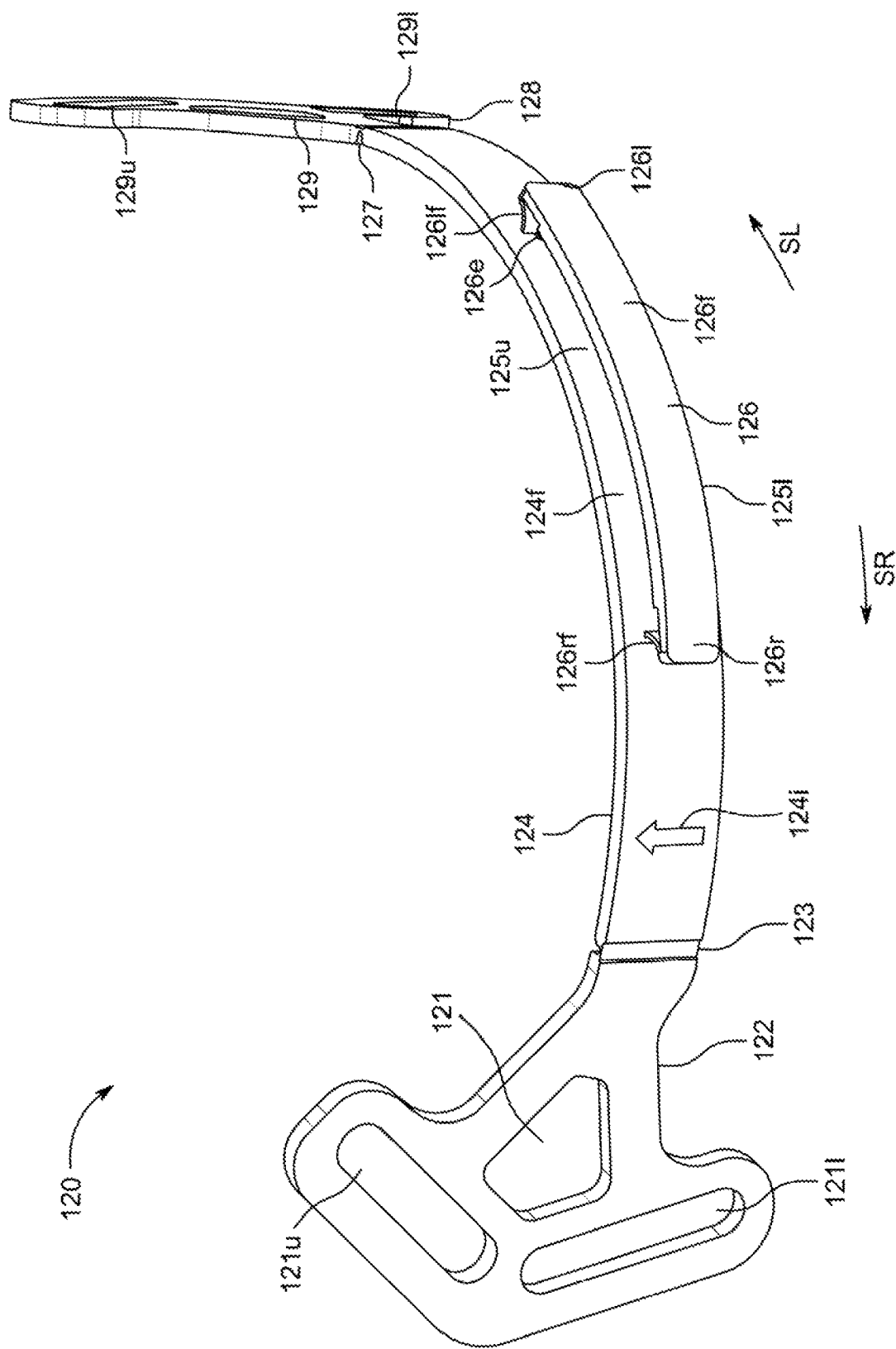
FIG. 7 is a front, right, top perspective view of a mount subassembly of the tube holding assembly of FIGS. 1-6.
Figure 8:
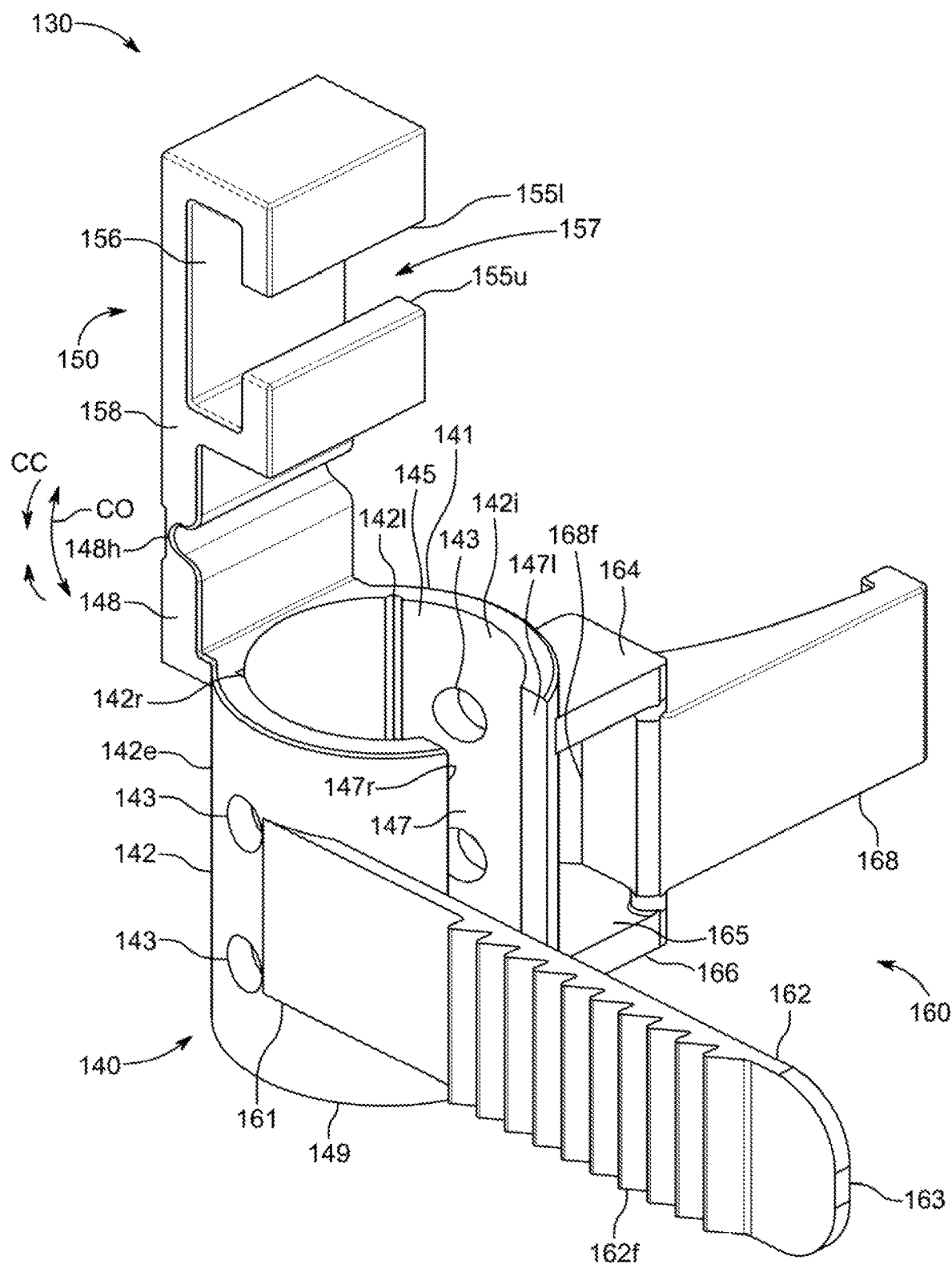
FIG. 8 is a front, right, top perspective view of a slider lock subassembly of the tube holding assembly of FIGS. 1-6.
Figure 9:
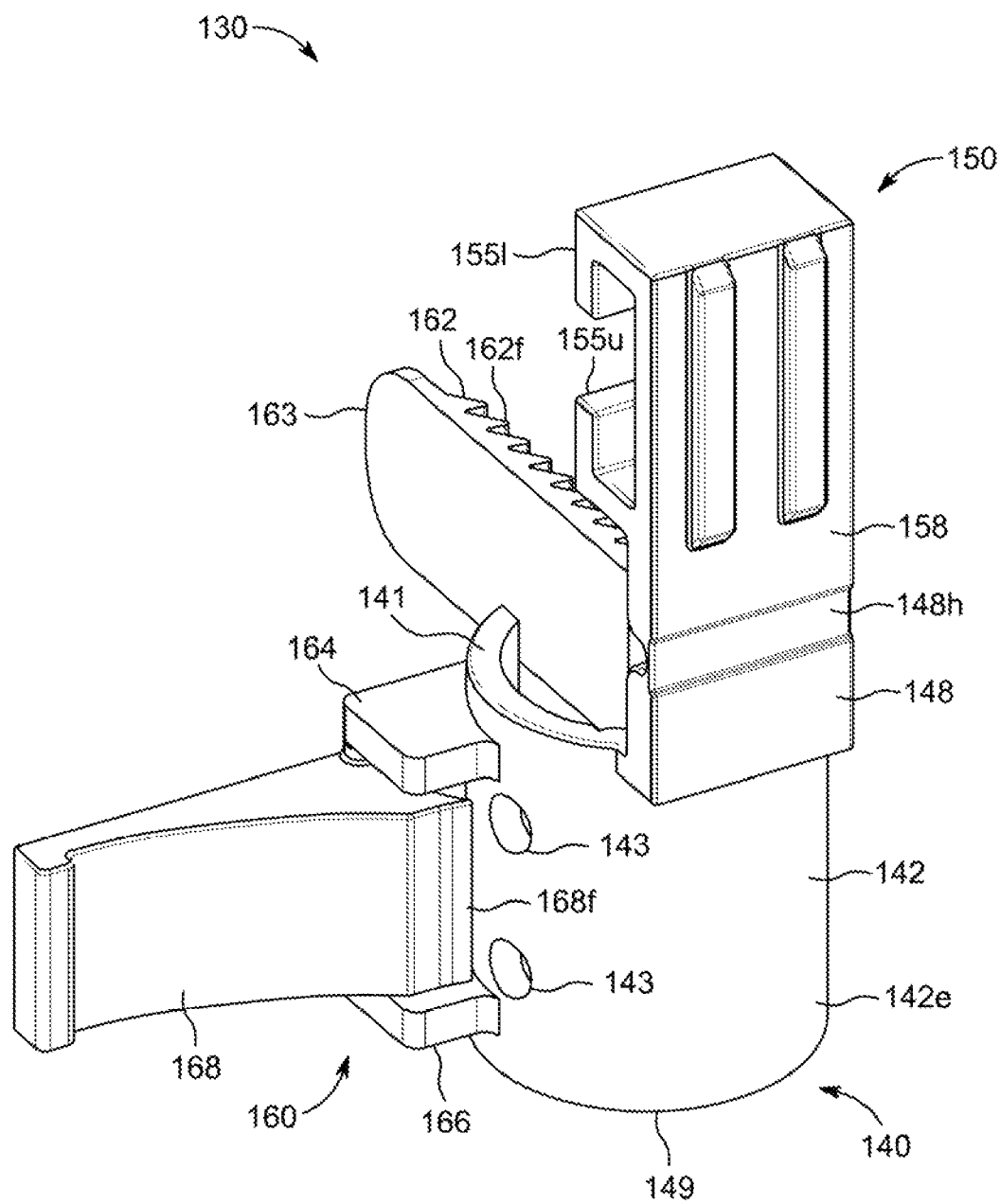
FIG. 9 is a rear, left, top perspective view of the slider lock subassembly of FIGS. 1-6 and 8.
Figure 10:
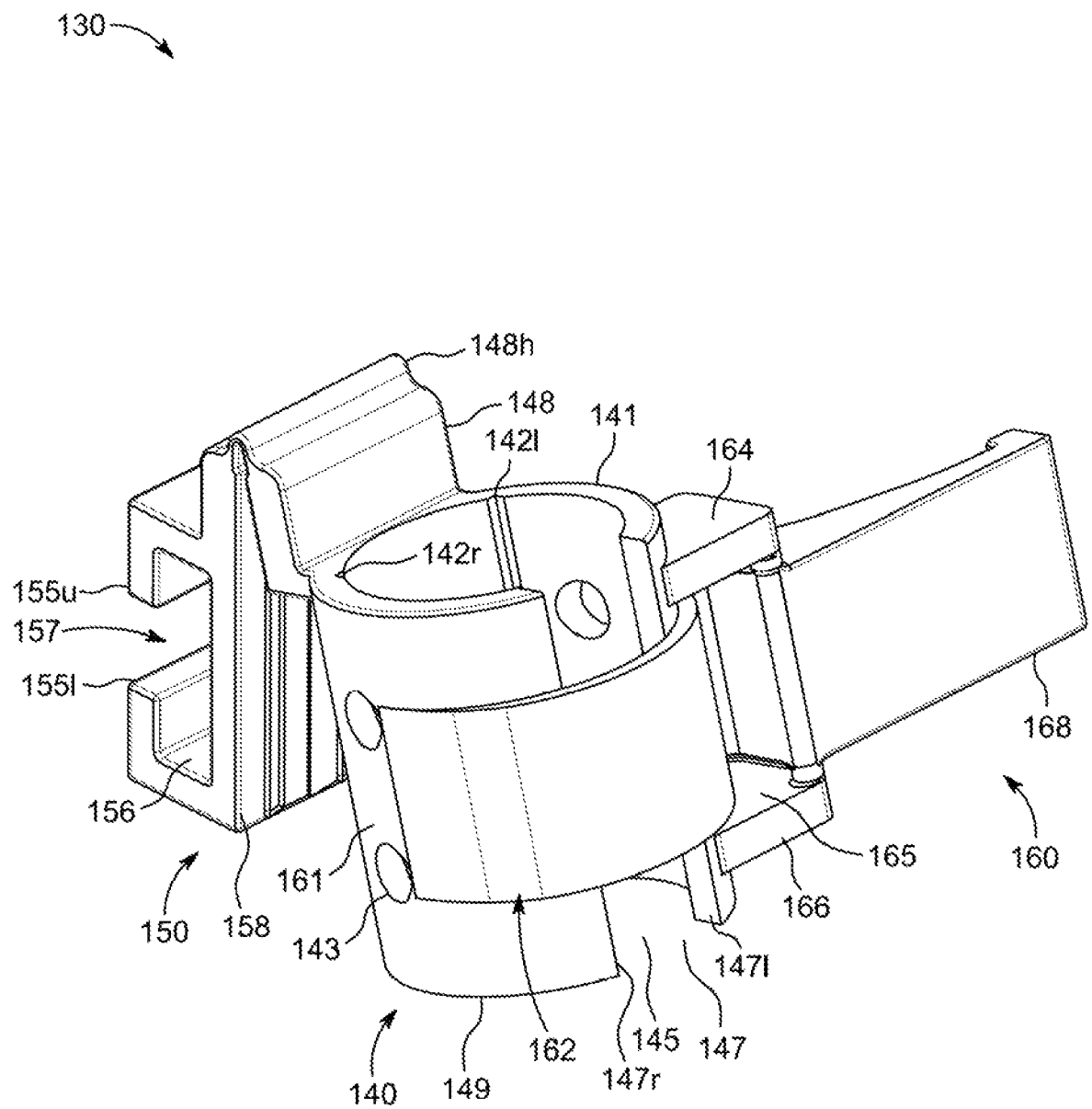
FIG. 10 is a front, right, top perspective view of the slider lock subassembly of FIGS. 1-6, 8, and 9, similar to FIG. 8 but with the slider lock subassembly closed.
Figure 11:
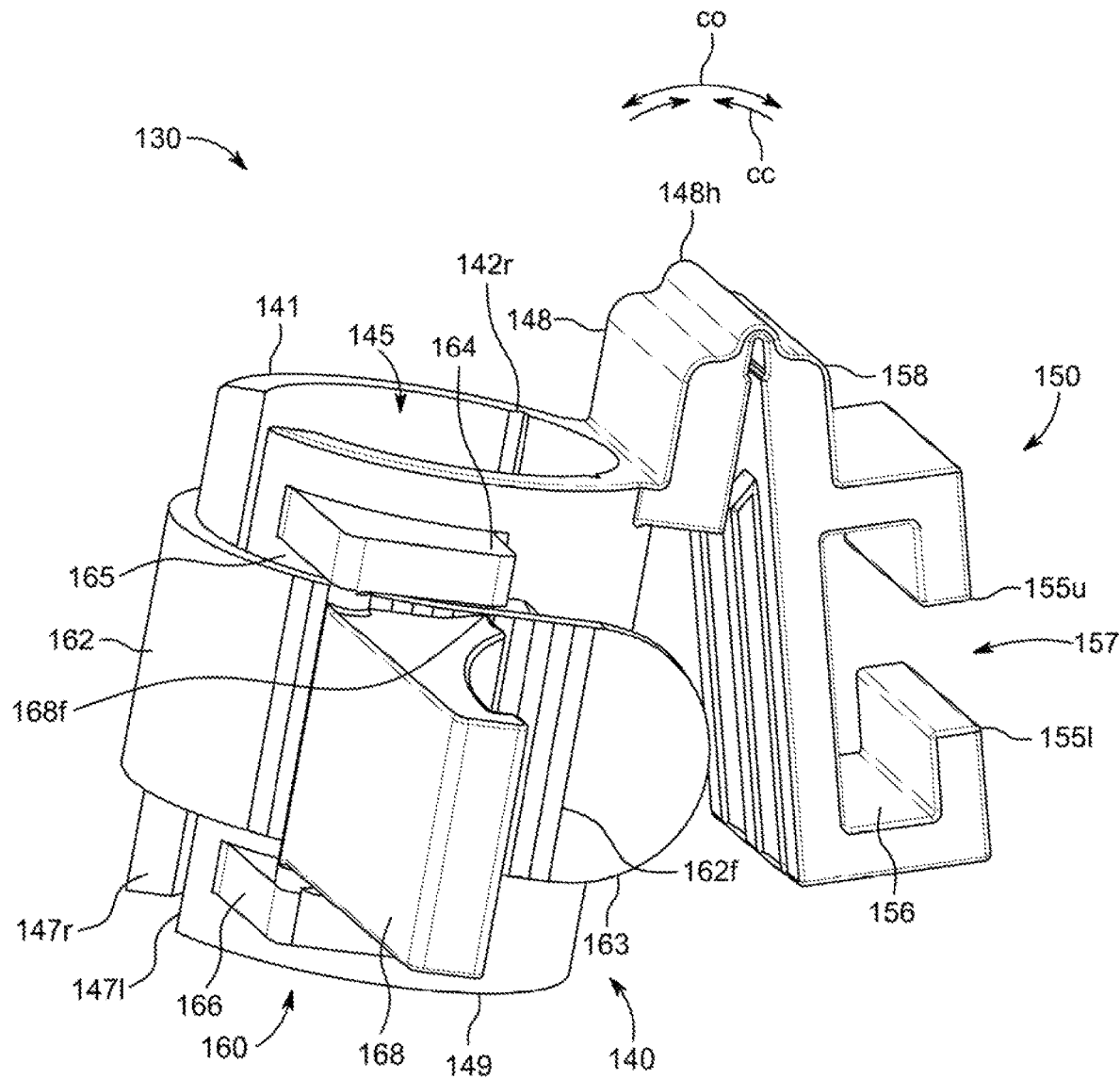
FIG. 11 is a left, top perspective view of the slider lock subassembly of FIGS. 1-6 and 8-10, with the slider lock subassembly closed.
Figure 12:
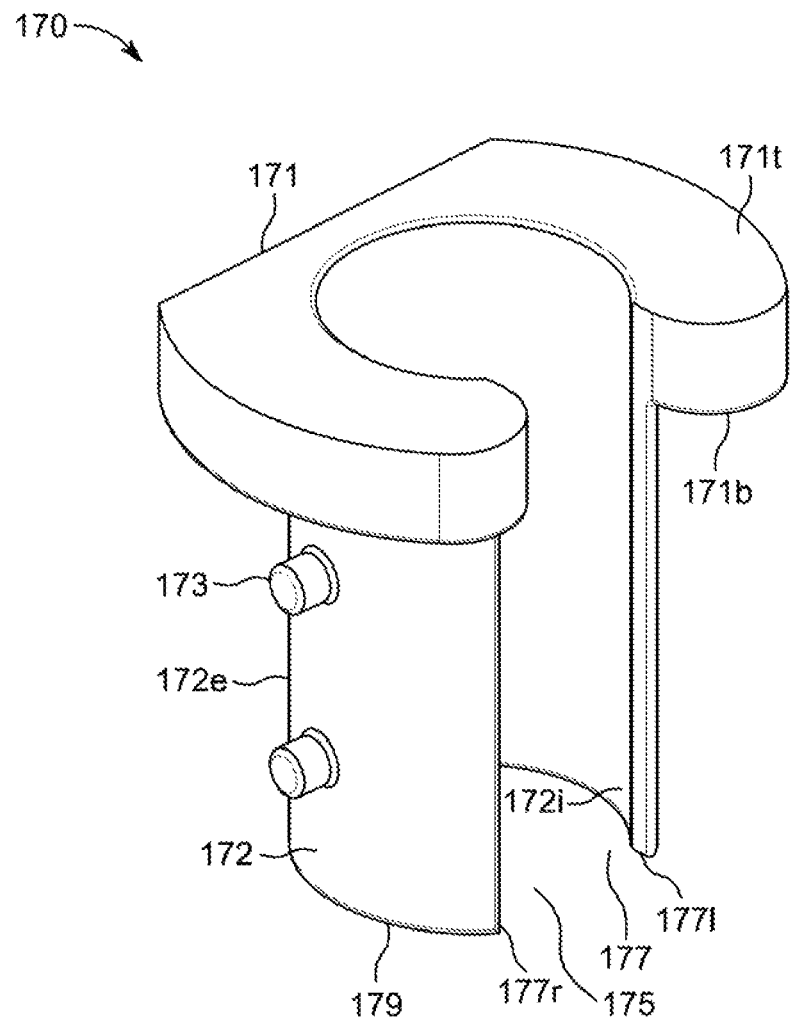
FIG. 12 is a front, right, top perspective view of a tube liner of the tube holding assembly of FIGS. 1-6.

FIGS. 1-3 show an illustrative system 1 including a tube holding assembly 100 that may be worn on a patient's head PH (e.g., a head with a right ear RE, a left ear LE, a mouth PM, a nose PN with a right nostril RN and/or a left nostril LN, and/or the like). Tube holding assembly 100, as shown in FIGS. 1-6 may include a tube 102, a strap subassembly 110, a mount subassembly 120 (e.g., as also shown in FIG. 7), a slider lock subassembly 130 (e.g., as also shown in FIGS. 8-11), and a tube liner 170 (e.g., as also shown in FIG. 12). Tube 102 may define a tube hollow passageway 102h, which may have an outer cross-sectional dimension (e.g., diameter) DP, extending between a proximal tube end 101 and a distal tube end 103. Tube 102 may be made of any suitable material(s), including polyurethane ("PU"), and may be introduced into a patient in any suitable manner for treating the patient in any suitable manner. As just one example, tube 102 may be used as a nasogastric ("NG") tube, where distal tube end 103 may be inserted up through a patient's nostril (e.g., right nostril RN or left nostril LN of patient's head PH), then down through the patient's esophagus, and then into the patient's stomach. Once distal tube end 103 is in such a functional position or any other suitable position with respect to the patient (e.g., positioned in a particular target space within the patient), other portions of assembly 100 may be used to hold tube 102 in that position with respect to the patient and such that proximal tube end 101, and, thus, passageway 102h, may be accessible to an operator of assembly 100 (e.g., a physician or nurse or perhaps even the patient itself) for use in introducing any suitable material (e.g., food, air, medication, any other suitable fluids, and/or the like) into the target space within the patient via tube passageway 102h and/or for use in removing any suitable material (e.g., stomach contents, air, any other suitable fluids, and/or the like) from the target space within the patient via tube passageway 102h. Therefore, in some particular embodiments, assembly 100 may use tube 102 as a nasogastric tube for use in carrying out any suitable procedures via a nostril of the patient (e.g., feeding and/or intubation and/or specimen removal). Alternatively, assembly 100 may use tube 102 as any other suitable tube for use in carrying out any suitable procedures via any other suitable orifice of the patient (e.g., patient's mouth PM).

As shown in FIGS. 1-6, when assembly 100 is fully assembled for use in holding tube 102 in a functional position with respect to patient's head PH (e.g., extending into one of nostrils LN or RN), a portion of tube 102 may be held within tube liner 170, which may be held within slider lock subassembly 130, which may be coupled to mount subassembly 120, which may be coupled to strap subassembly 110, which may be coupled to patient's head PH. Strap subassembly 110 and mount subassembly 120, when coupled together, may be adjusted or manipulated in any suitable manner to fasten or secure or hold mount subassembly 120 in a particular position with respect to patient's head PH in a stable and/or tight and/or comfortable manner. Any suitable holder or strap subassembly 110 may be provided for coupling to and holding or securing or fastening any suitable mount subassembly 120 on patient's head PH (e.g., at a particular position with respect to head PH). For example, in some embodiments, as shown, strap subassembly 110 may include a strap base 110b from which may extend a lower right strap 112 to a lower right strap end 111, an upper right strap 114 to an upper right strap end 113, a lower left strap 116 to a lower left strap end 115, an upper left strap 118 to an upper left strap end 117, and/or a top strap 119, while mount subassembly 120 may include a mount base 124 extending between a right mount end 122 with at least one right mount end strap opening 121, and a left mount end 128 with at least one left mount end strap opening 129. An indicator 124i may be provided to indicate to an operator an intended orientation for use. As shown, for example, lower right strap end 111 of lower right strap 112 may be passed through a lower right mount end strap opening 121l and pulled back towards and coupled to a portion of strap subassembly 110 (e.g., another portion of lower right strap 112) for coupling mount subassembly 120 to lower right strap 112, upper right strap end 113 of upper right strap 114 may be passed through an upper right mount end strap opening 121u and pulled back towards and coupled to a portion of strap subassembly 110 (e.g., another portion of upper right strap 114) for coupling mount subassembly 120 to upper right strap 114, lower left strap end 115 of lower left strap 116 may be passed through a lower left mount end strap opening 129l and pulled back towards and coupled to a portion of strap subassembly 110 (e.g., another portion of lower left strap 116) for coupling mount subassembly 120 to lower left strap 116, and/or upper left strap end 117 of upper left strap 118 may be passed through an upper left mount end strap opening 129u and pulled back towards and coupled to a portion of strap subassembly 110 (e.g., another portion of upper left strap 118) for coupling mount subassembly 120 to upper left strap 118.

Figure 4:
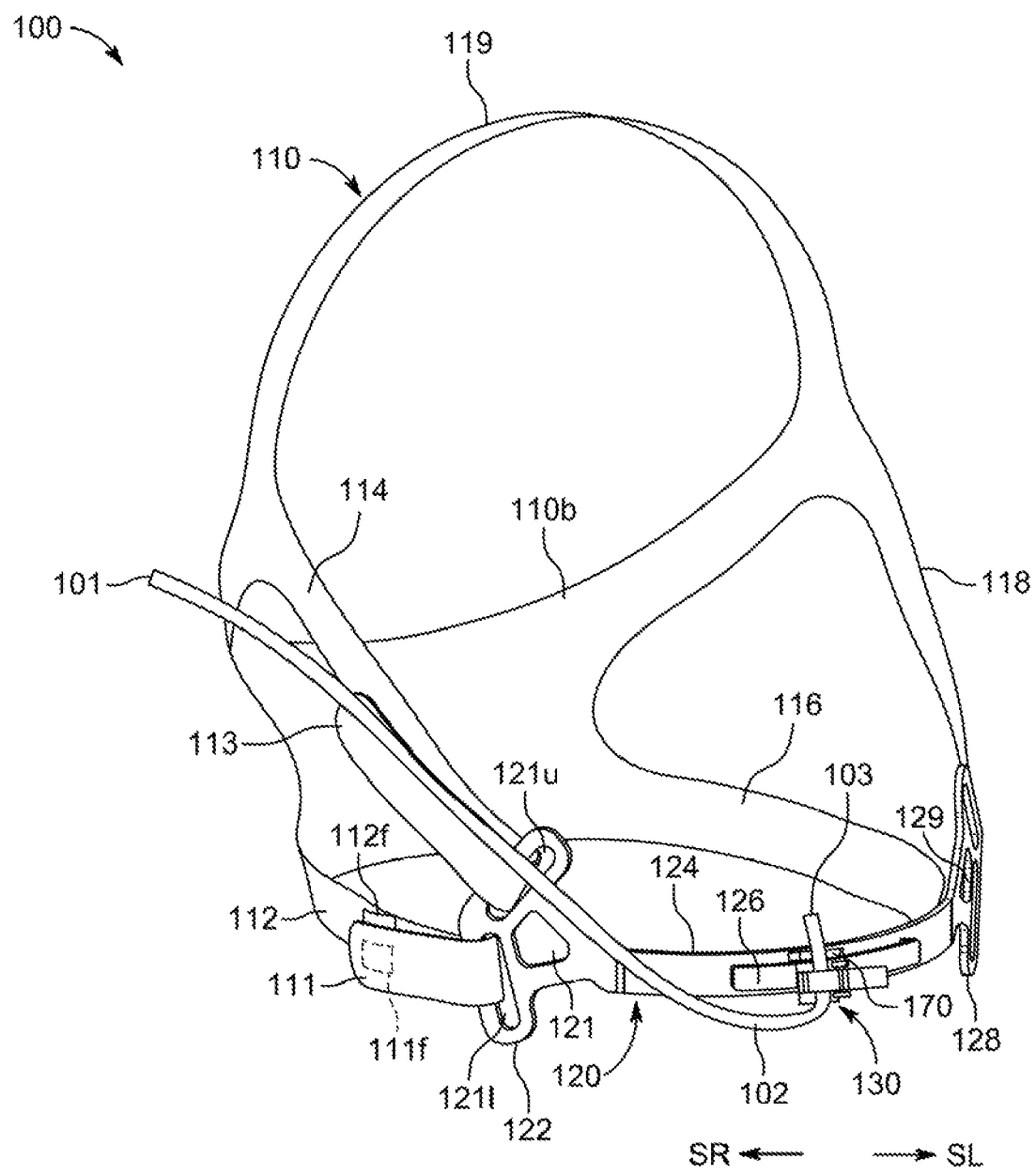
FIG. 4 is a front, right, top perspective view of the tube holding assembly of FIGS. 1-3.
Figure 5:
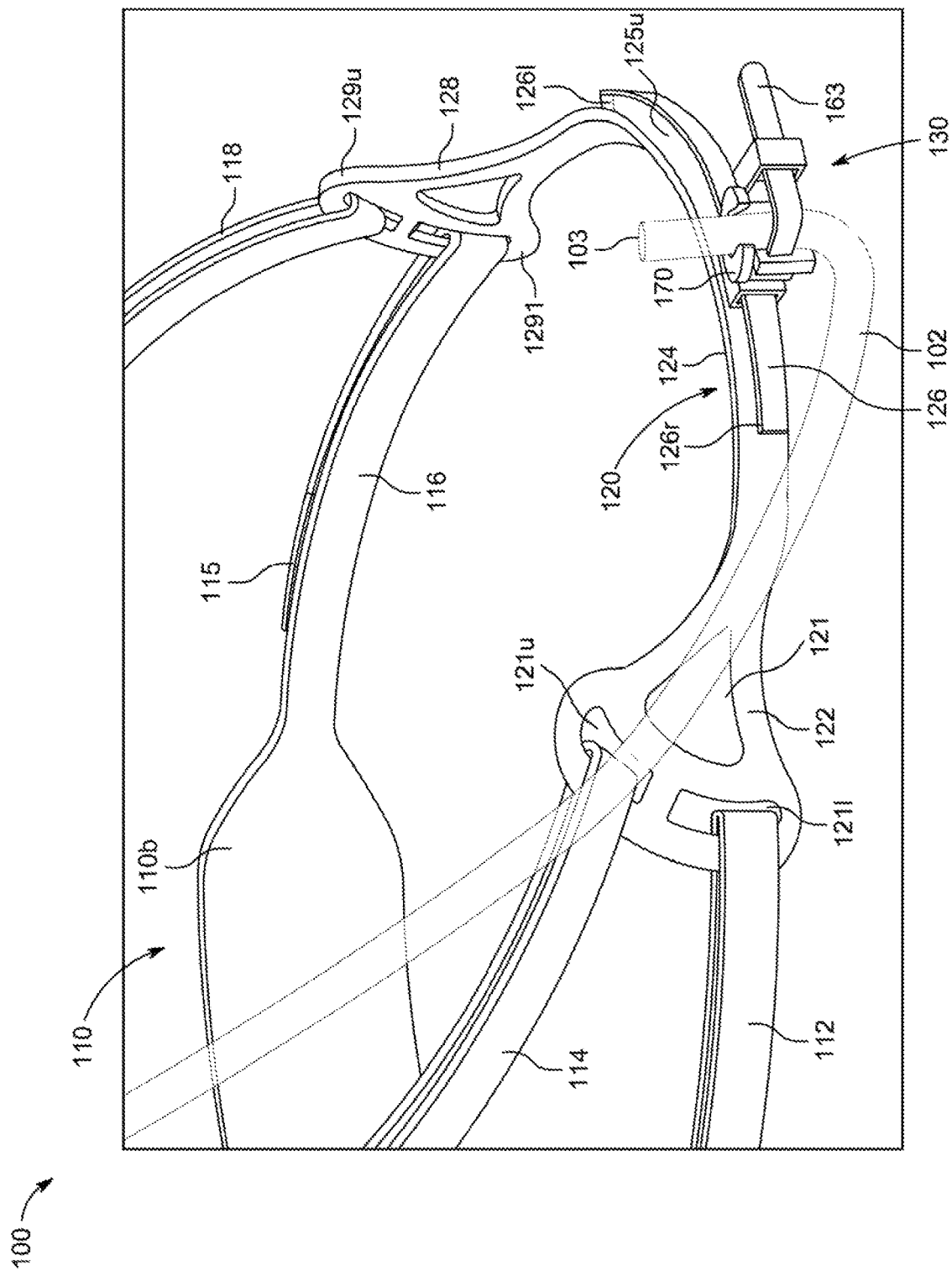
FIG. 5 is a front, right, top perspective view of a portion of the tube holding assembly of FIGS. 1-4.
Figure 6:
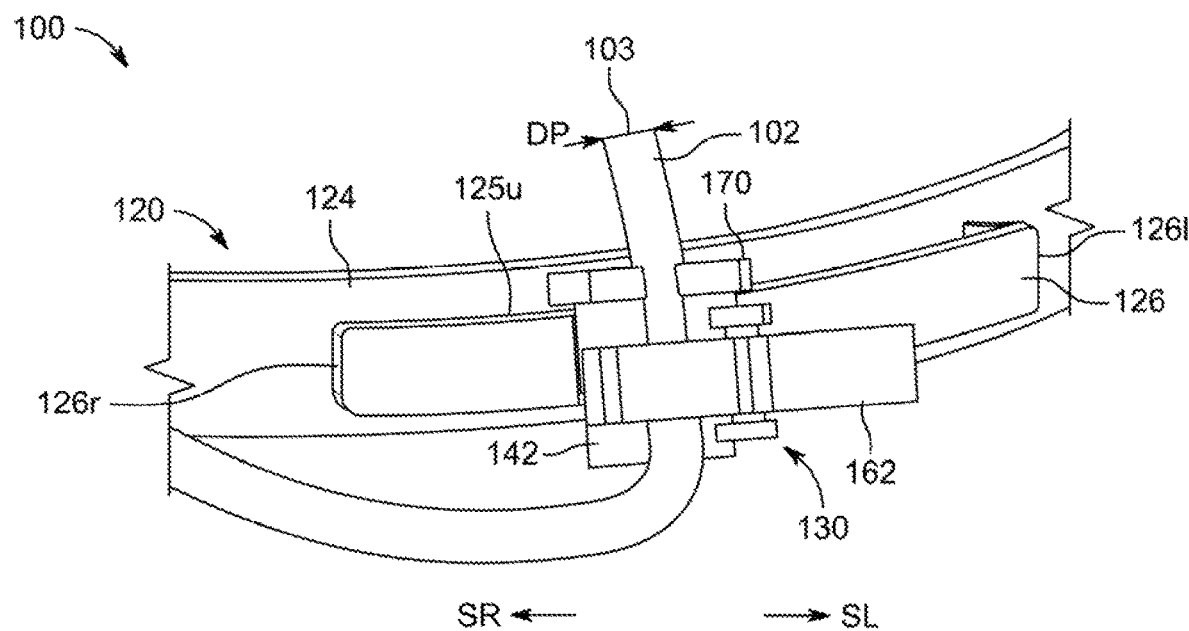
FIG. 6 is a front, right, top perspective view of a portion of the tube holding assembly of FIGS. 1-5.
Figure 16:
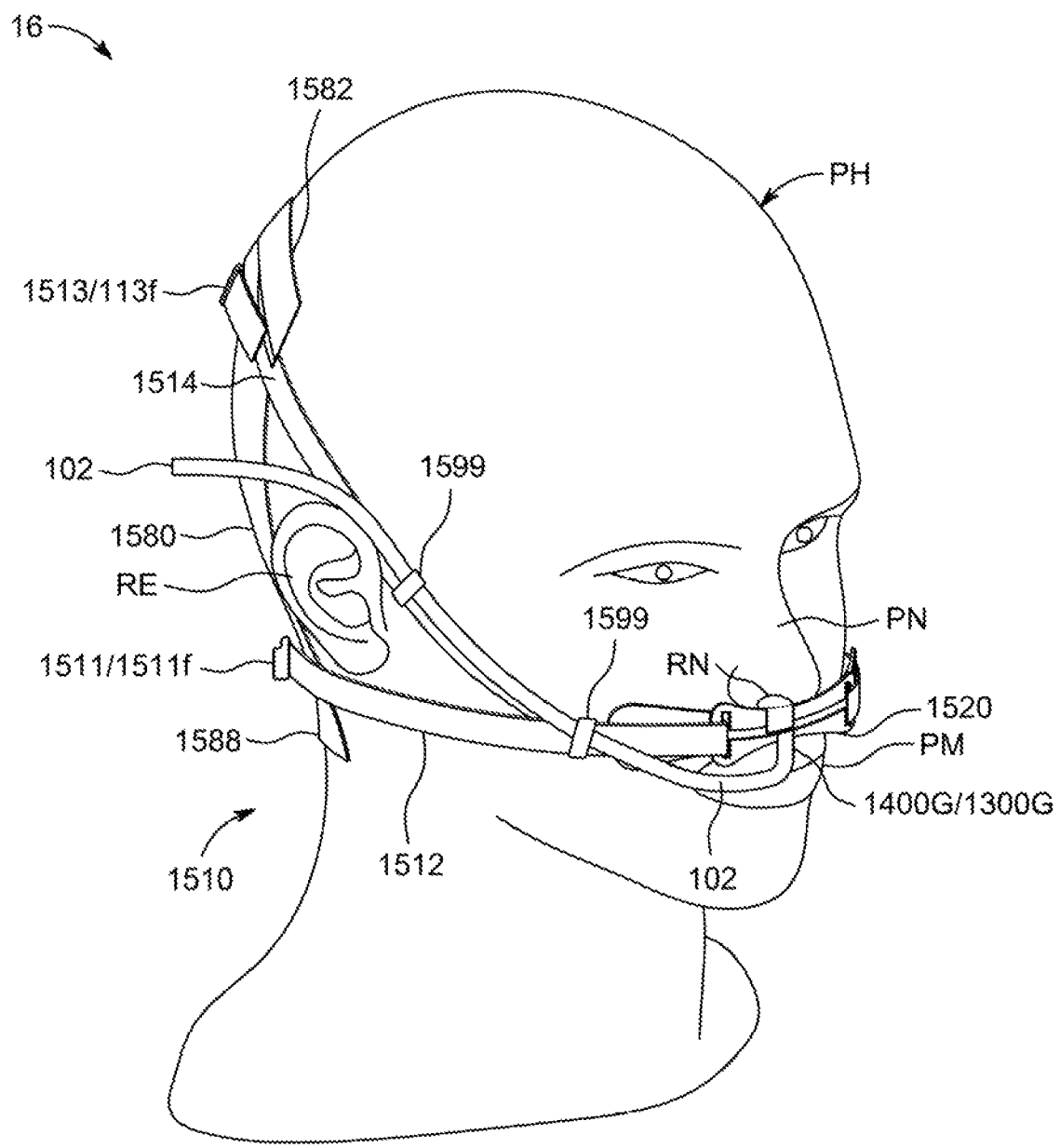
FIG. 16 is a front, right, top perspective view of another system including the patient of FIGS. 1-3 wearing the tube holding assembly of FIGS. 15A-15C.
Figure 17A:
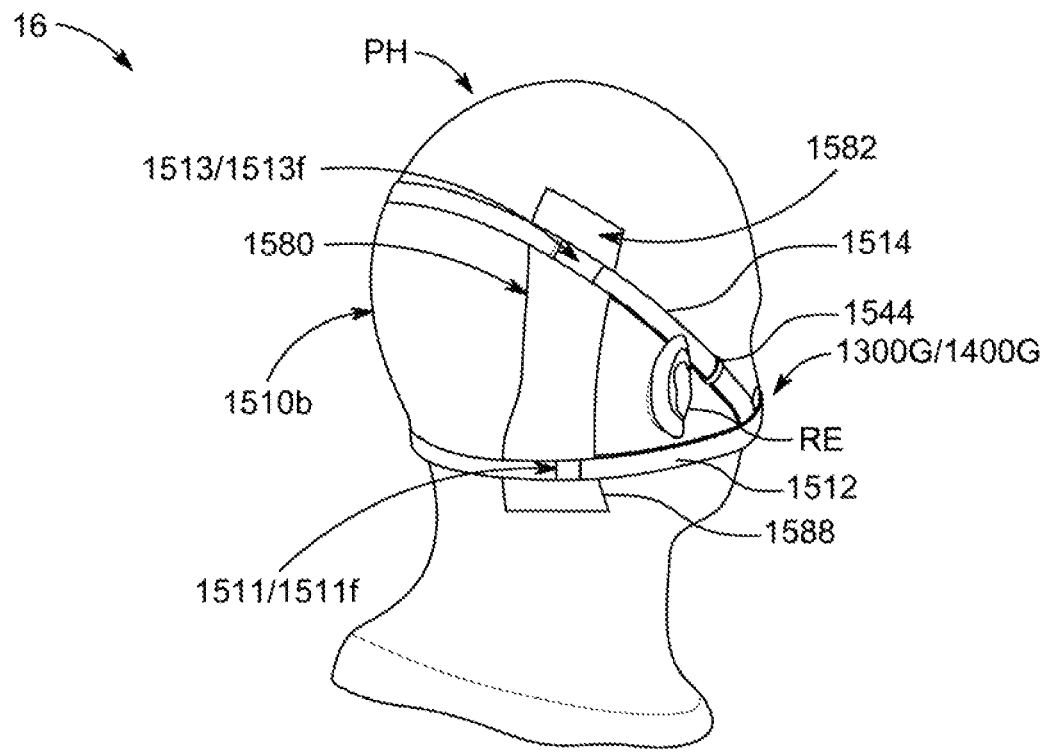
FIG. 17A is a rear, right, top perspective view of the patient of FIGS. 1-3 and 16 wearing the tube holding assembly of FIGS. 15A-15C and 16, with protective flaps open.
Figure 17B:
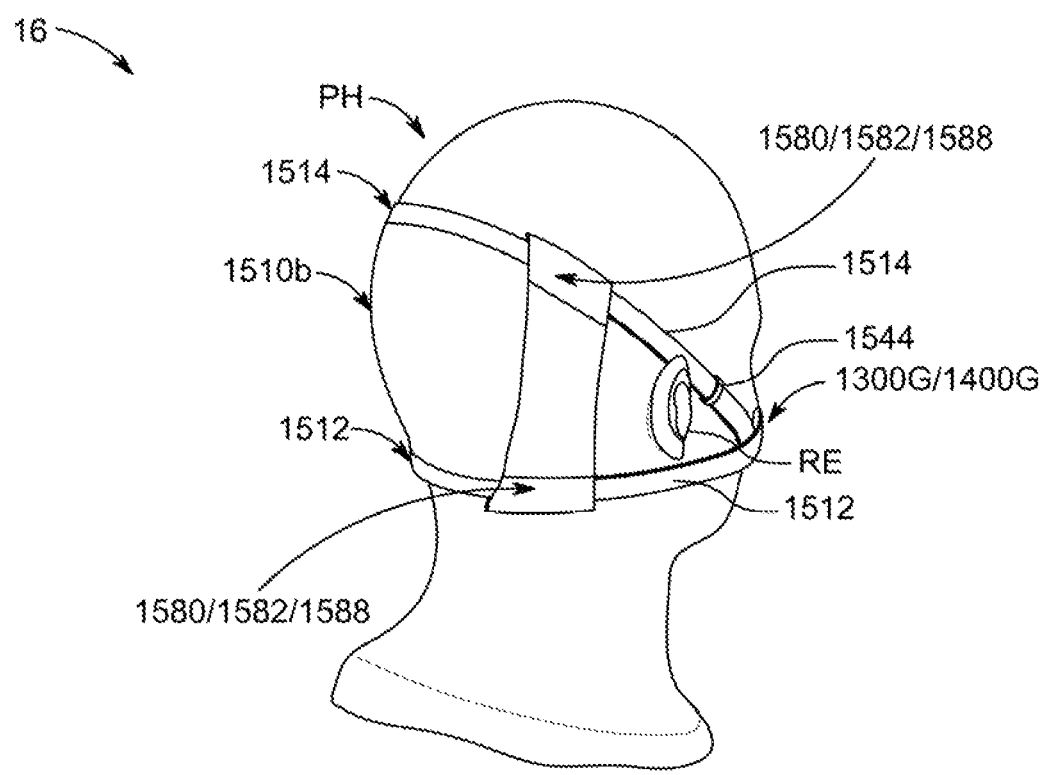
FIG. 17B is a rear, right, top perspective view of the patient of FIGS. 1-3, 16, and 17A wearing the tube holding assembly of FIGS. 15A-15C, 16, and 17A, with protective flaps closed.

Each one of straps 112, 114, 116, and 118 may be provided with at least one set of coupling features for enabling the length of each strap to be adjusted. For example, as shown in FIG. 4, strap 112 may include at least one coupling feature 112*f* along at least a portion of a length of strap 112 while strap 112 may also include at least one other coupling feature 111*f* at or adjacent strap end 111, such that features 111*f* and 112*f* may be coupled to one another for maintaining a particular length of strap 112 to be extending between strap base 110*b* and mount subassembly 120 (e.g., opening 121*l*). For example, such coupling features 111*f* and 112*f* may be different but interlocking components of a hook and loop fastener assembly (e.g., Velcro™), thereby enabling strap end 111 to be removably coupled to another portion of strap 112 for easily adjusting the length of strap 112 extending between base 110*b* and mounting subassembly 120. Any other suitable coupling features may be used, including, but not limited to, snaps, clips, click fit strap connectors, a slide strap adjuster, any suitable adjuster buckle, and/or the like. In some embodiments, such as shown in FIGS. 16, 17A, and 17B with respect to a system 16 with another assembly, one or more protective flaps may be used to cover one, some, or each of the coupling features of one, some, or each strap, such that a patient may not easily access the coupling features for readjusting the fit of the assembly or for perhaps removing the assembly altogether.

The length of each one of straps 112, 114, 116, and 118 extending between strap base 110*b* and mount subassembly 120 may be independently adjusted based on the size and shape of patient's head PH (e.g., by varying the position at which a strap's free end is coupled to another portion of strap subassembly 110 after passing through an opening of a mount subassembly 120), which may allow for tube holding assembly 100 to be securely yet comfortably worn on any suitably sized patient's head PH. When each one of straps 112, 114, 116, and 118 may be coupled to mount subassembly 120 in such a manner, mount base 124 may be securely yet comfortably held underneath patient's nose PN (e.g., above and along the upper lip of patient's mouth PM) while at least a portion of strap base 110*b* may be held against a portion of the back of patient's head PH, as lower right strap 112 may extend between base 110*b* and mount base 124 underneath the patient's right ear RE, as upper right strap 114 may extend between base 110*b* and mount base 124 above the patient's right ear RE, as lower left strap 116 may extend between base 110*b* and mount base 124 underneath the patient's left ear LE, as upper left strap 118 may extend between base 110*b* and mount base 124 above the patient's left ear LE, and/or as top strap 119 may extend over the top of patient's head PH.

Each one of straps 112, 114, 116, 118, 119, and/or base 110*b* may be made of any suitable material, including, but not limited to, nylon, cloth, mesh, foam, and/or the like, and may include any suitable comfort material provided on an inner surface of one or more of the straps or base that may interface with a portion of patient's head PH (e.g., a foam layer that may be adhered to an inner surface of each strap for providing a comfortable interface between strap subassembly 110 and patient's head PH when tube holding assembly 100 is held in an appropriate position on patient's head PH). A length of top strap 119 may be adjustable using any suitable mechanism (e.g., similar to one of the other straps, but through an opening in one of the upper straps or around an upper strap) or may be made of an elastic material in order to stretch or contract for making appropriate contact with a top of patient's head PH. In other embodiments, lower right strap 112 and upper right strap 114 may each extend from different portions of strap base 110*b* to a single right strap end (not shown) that may be passed through a single right mount end strap opening 121 for enabling adjustment with respect to mount subassembly 120, while lower left strap 116 and upper left strap 118 may each extend from different portions of strap base 110*b* to a single left strap end (not shown) that may be passed through a single left mount end strap opening 129 for enabling adjustment with respect to mount subassembly 120. In yet other embodiments, strap base 110*b* may not exist, and a lower strap may extend between lower right strap end 111 and lower left strap end 115, while an upper strap, distinct from such a lower strap, may extend between upper right strap end 113 and upper left strap end 117, while top strap 119 may extend between different portions of such an upper strap, or may not be provided at all. Any other suitable additional or alternative mechanisms may be provided by strap subassembly 110 or otherwise for holding mount subassembly 120 in a particular position with respect to patient's head PH.

Mount subassembly 120 may include one or more hinge elements (e.g., one or more living hinges) along its length for enabling mount subassembly to flex or curve along a portion of patient's head PH. For example, as shown, a right mount hinge 123 may be provided between mount base 124 and right mount end 122, and/or a left mount hinge 127 may be provided between mount base 124 and left mount end 128, where such hinge(s) may enable the shape of mount subassembly 120 between ends 122 and 128 bend or flex to suit different heads of different shapes and sizes (e.g., hinge 123 may enable right mount end 122 to form any suitable angle with respect to an adjacent portion of mount base 124 such that end 122 may extend along a portion of a side of a patient's face while base 124 may extend along a portion of a front of a patient's face). Mount subassembly 120 may also include a slider clamp mount track body 126 that may extend between a slider clamp mount track left end 126*l* and a slider clamp mount track right end 126*r*. Track body 126 may include an extension ledge 126*e* extending forwardly out from a front face 124*f* of mount base 124, while a front wall 126*f* of track body 126 may extend upwardly and/or downwardly (e.g., perpendicularly) from a front of extension ledge 126*e*, while a right lock 126*rf* (e.g., flexible flap) may extend backward from front wall 126*f* at right end 126*r* towards front face 124*f* of mount base 124, and/or while a left lock 126*lf* (e.g., flexible flap) may extend backward from front wall 126*f* at left end 126*l* towards front face 124*f* of mount base 124. Such a structure may create a slider clamp mount track space, such as a lower slider clamp mount track space 125*l* between front face 124*f* of mount base 124 and a rear surface of front wall 126*f* below extension ledge 126*e* as extending between locks 126*rf* and 126*lf*, and/or such as an upper slider clamp mount track space 125*u* between front face 124*f* of mount base 124 and a rear surface of front wall 126*f* above extension ledge 126*e* as extending between locks 126*rf* and 126*lf*. One or both of such locks 126*rf* and 126*lf* may be flexible for enabling access to one or both of track spaces 125*u* and 125*l* by one or more features of a slider clamp 150 of slider lock subassembly 130 (e.g., one or both of upper slider clamp feature 155*u* and lower slider clamp feature 155*l*, respectively, of clamp 150), such that slider lock subassembly 130 (e.g., when holding or about to hold tube 102) may be able to be held close to but also slide along mount base 124 (e.g., in the direction of slide left arrow SL of the track and/or in the direction of slide right arrow SR of the track). A rear face opposite front face 124*f* of mount base 124 may be operative to interface with (e.g., be held against) a portion of patient's head PH (e.g., above and/or along an upper lip of patient's mouth PM and/or just below and/or adjacent patient's nose PN).

Mount subassembly 120 may be made of any suitable material(s) through any suitable procedures, including, but not limited to, molded plastic, metal, and/or the like. At least a portion of mount base 124 may be provided by a material with enough rigidity to provide a mount track space(s) that may allow slider lock assembly 130 to slide therein for aligning with any suitable feature(s) of the patient (e.g., with a particular one of nostrils RN and LN) and/or to enable strap subassembly 110 to hold mount subassembly 120 in a particular position with respect to patient's head PH. Additionally, in some embodiments, mount subassembly 120 may include any suitable comfort material provided on a surface of mount base 124 that may interface with a portion of patient's head PH (e.g., a cushioning foam layer that may be adhered to mount base 124 (e.g., along the face opposite front face 124*f*) for providing a comfortable interface between mount base 124 and patient's head PH (e.g., the upper lip of patient's mouth PM) when tube holding assembly 100 is held in an appropriate position on patient's head PH). Mount base 124 may be any suitable size (e.g., 19 centimeters in length) for use with any suitable size patient. Different size assembly components may be used for different size patients.

Slider lock subassembly 130 may include a tube clamp 140, a slider clamp 150, and a tube adjuster 160. Tube clamp 140 may include a tube clamp body 142 of any suitable shape. For example, as shown, tube clamp body 142 may have a substantially hollow cylindrical shape, with a tube clamp body exterior wall surface 142*e* and a tube clamp body interior wall surface 142*i* extending between a tube clamp body top 141 and a tube clamp body bottom 149 for defining a hollow tube clamp body passageway 145 that may be accessible via top 141 and/or bottom 149, as well as via a tube clamp body opening 147 that may extend along a length of body 142 between a tube clamp body left edge 147*l* and a tube clamp body right edge 147*r*. One or more hinges, such as a tube clamp body left hinge 142*l* and/or a tube clamp body right hinge 142*r*, may be provided along the length of body 142 (e.g., along a length of tube clamp body interior wall surface 142*i*) for enabling the width of tube clamp body opening 147 between edges 147*l* and 147*r* to expand or contract, thereby expanding or contracting a cross-sectional area or any suitable cross-sectional dimension(s) of hollow tube clamp body passageway 145, which may allow any suitable component(s) (e.g., tube 102 with or without tube liner 170) to be loosely positioned therein and then clamped tightly therein.

Tube adjuster 160 may be coupled to tube clamp 140 for selectively expanding or contracting or maintaining a cross-sectional area or any suitable cross-sectional dimension(s) of hollow tube clamp body passageway 145. For example, as shown, tube adjuster 160 may include a tube adjuster tie 162 extending between a tube adjuster tie fixed end 161, which may be coupled to a portion of exterior wall surface 142*e* of tube clamp body 142 adjacent tube clamp body right edge 147*r*, and a tube adjuster tie free end 163. Additionally, as shown, tube adjuster 160 may include a pawl 168 rotatably or otherwise movably coupled between a pawl top 164 and a pawl bottom 166, each of which may be coupled to a portion of exterior wall surface 142*e* of tube clamp body 142 adjacent tube clamp body left edge 147*l*, such that at least one pawl feature 168*f* of pawl 168 may be positioned within a pawl opening 165 that may be defined between pawl 168 and pawl top 164 and pawl bottom 166 and tube clamp body 142. Tube adjuster 160 may be manipulated (e.g., by any suitable operator of assembly 100) between an open configuration of FIGS. 8 and 9 and a closed configuration of FIGS. 1-6, 10, and 11 by passing tube adjuster tie free end 163 across and beyond tube clamp body opening 147 and into pawl opening 165, whereby any suitable tube adjuster tie feature(s) 162*f* that may be provided along a surface of tube adjuster tie 162 may be engaged by any suitable pawl feature(s) 168*f* for holding tube adjuster tie 162 at a particular position within and with respect to pawl opening 165 and pawl feature(s) 168*f*. The further tube adjuster tie 162 may be inserted into opening 165, the more a cross-sectional dimension (e.g., periphery) of hollow tube clamp body passageway 145 may contract. Tube adjuster tie feature(s) 162*f* and pawl feature(s) 168*f* may interact to engage and retain tube adjuster tie 162 in a particular position within opening 165 and may be configured only to let tie 162 be further inserted into opening 165 but not to let tie 162 be removed from opening 165 unless pawl 168 is used to release the engagement of pawl feature(s) 168*f* from tube adjuster tie feature(s) 162*f*. Therefore, an assembly operator may be enabled to ratchet tie 162 further into and through opening 165 for tightening a clamping of any suitable component(s) within tube clamp body passageway 145. Any suitable mechanisms in addition to or as an alternative to a ratchet and pawl mechanism may be used to enable such controlled contracting and expanding and maintaining of the dimension(s) of tube clamp body passageway 145.

Slider clamp 150 may include a slider clamp body 158 that may be any suitable shape for defining any suitable slider clamp body passageway 156 of any suitable shape. For example, as shown, slider clamp body 158 may define a T-shaped slider clamp body passageway 156 extending through a slider clamp body opening 157 between a lower slider clamp feature 155*l* of slider clamp body 158 and an upper slider clamp feature 155*u* of slider clamp body 158. Slider clamp 150 may be coupled to a tube clamp body slider extension 148 of tube clamp 140 (e.g., as may be coupled to tube clamp body 142 adjacent tube clamp body top 141), such as via a tube clamp body slider extension hinge 148*h*, for enabling slider clamp 150 to be moved (e.g., rotated, bent, etc.) with respect to tube clamp 140 (e.g., about hinge 148*h*) between an open configuration of FIGS. 8 and 9 and a closed configuration of FIGS. 1-6, 10, and 11 or anywhere in between (e.g., in the direction of clamp close arrows CC or in the direction of clamp open arrows CO). Hinge 148*h* may be any suitable mechanical bearing that may allow any suitable movement between clamp body 142 and clamp body 158 (e.g., an ideal hinge or any other suitable hinge) that may be made of one or more suitable flexible materials and/or any suitable moving components. As just one example, hinge 148*h* may be a living hinge. As shown, at least one of locks 126*rf* and 126*lf* of mount subassembly 120 may be flexible for enabling access by one or each of upper slider clamp feature 155*u* and lower slider clamp feature 155*l* of clamp 150 to a respective one of track spaces 125*u* and 125*l*. This may enable slider clamp 150 to be held within track spaces 125 and between locks 126*rf* and 126*lf* of mount subassembly 120 such that slider lock subassembly 130 (e.g., when in a closed position of FIGS. 1-6, 10, and 11 (e.g., when holding or about to hold tube 102)) may be held close to mount base 124 but also allowed to slide along mount base 124 (e.g., in the direction of slide left arrow SL and/or in the direction of slide right arrow SR). It is to be understood that the slide directions SL and SR of slider clamp body 158 with respect to the track of mount subassembly 120 may be axially opposite each other or opposite each other along a curved track (e.g., as shown) such that the directions of arrows SL and SR may be linearly opposite each other at any given point of body 158 along a curved track but the directions may be curved along the length of the track.

Tube liner 170 may include a tube liner body 172 of any suitable shape. For example, as shown, tube liner body 172 may have a substantially hollow cylindrical shape, with a tube liner body exterior wall surface 172e and a tube liner body interior wall surface 172i extending between a tube liner body top 171 and a tube liner body bottom 179 for defining a hollow tube liner body passageway 175 that may be accessible via top 171 and/or bottom 179, as well as via a tube liner body opening 177 that may extend along a length of body 172 between a tube liner body left edge 177l and a tube liner body right edge 177r. Tube liner body 172 may be made of any suitable material, such as silicone or foam and/or the like, or may be provided with one or more hinges, for enabling the width of tube liner body opening 177 between edges 177l and 177r to expand or contract, thereby expanding or contracting a cross-sectional area or any suitable cross-sectional dimension(s) of hollow tube liner body passageway 175, which may allow any suitable component(s) (e.g., tube 102) to be loosely positioned therein and then clamped tightly therein. Therefore, tube liner body 172 may be configured to function similarly to tube clamp body 142, but may be provided to provide a more soft or forgiving interface with tube 102 (e.g., to prevent tearing or kinking or pinching material of tube 102 and/or to prevent slider lock subassembly 130 from limiting the size of tube hollow 102h such that fluid may flow freely therethrough) than may be provided by tube clamp body 142. When tube adjuster 160 is used to tighten (e.g., ratchet) tube clamp 140, liner body 172 may more tightly grab onto and/or squeeze onto and/or gently but more firmly hold tube 102. Alternatively, tube liner body 172 may not be needed and tube 102 may be positioned within and clamped directly by tube clamp body 142. However, if used, as shown, tube liner body 172 may include one or more tube liner body clamp features 173 that may extend outwardly from tube liner body exterior wall surface 172e of tube liner body 172 and that may be operative to engage or otherwise interact with one or more respective tube clamp body liner features 143 that may extend inwardly into tube clamp body interior wall surface 142i of tube clamp body 142, such that tube liner body 172 may not move with respect to tube clamp body 142 (e.g., out from either the top or bottom of tube clamp body 142 (e.g., when a tugging force is applied to tube 102)). Moreover, as shown, tube liner body top 171 of tube liner 170 may be larger than (e.g., extend upwardly and outwardly from) tube liner body 172 between a top surface 171t and a bottom surface 171b. Bottom surface 171b may be operative to rest against tube clamp body top 141 of tube clamp body 142, while top surface 171t may be operative to support or interface with a bottom of patient's nose PN when assembly 100 is being worn by patient's head PH. With or without tube liner 170, tube adjuster 160 and tube clamp 140 may be configured to clamp and hold different tubes with different tube hollows of different cross-sectional dimensions (e.g., tube 102 with hollow 102h of dimension DP and/or tube 102' with hollow 102h' of dimension DP' that may be greater than DP by any suitable magnitude (e.g., 18 Fr. (e.g. 6.0 millimeters) versus 16 Fr. (e.g. 5.3 millimeters) versus 14 Fr. (e.g. 4.7 millimeters) versus 12 Fr. (e.g. 4.0 millimeters) versus 10 Fr. (e.g. 3.2 millimeters) or the like)).

Therefore, as shown, when worn by patient's head PH, slider lock subassembly 130, with or without tube liner 170, may clamp a portion of tube 102 securely within passageway 145 of tube clamp 140 of slider lock subassembly 130 without limiting fluid flow through tube hollow 102h of that tube portion, while slider clamp 150 may movably couple slider lock subassembly 130 to mount subassembly 120 (e.g., such that slider lock subassembly 130 may be free to slide at least slightly in the direction of each one of slide left arrow SL and slide right arrow SR with respect to slider clamp mount track body 126 when slider clamp 150 is mated with slider clamp mount track body 126 within spaces 125l and 125u), and while strap subassembly 110 may hold mount subassembly 120 in a particular position with respect to patient's head PH. Therefore, when properly worn, assembly 100 may enable certain sliding movement of subassembly 130 and tube 102 with respect to mount subassembly 120 (e.g., in the direction of arrow SL and/or in the direction of arrow SR along track body 126) and/or certain rotational movement of tube clamp 140 and tube 102 with respect to mount subassembly 120 (e.g., in the direction of arrow CC and/or in the direction of arrow CO about hinge 148h), while tube 102 may be fixed to tube clamp 140 and while mount subassembly 120 may be substantially fixed with respect to patient's head PH.

Therefore, when tube 102 may be used as a nasogastric tube and may be introduced into the patient via a nostril, assembly 100 may be used to prevent proximal or distal migration of tube 102 with respect to the patient once inserted into the patient. Assembly 100 may also be used to prevent the patient from pulling tube 102 out from within the patient (e.g., intentionally or accidentally). Assembly 100 may be used to maintain a position of tube 102 after insertion of tube 102 into the patient, which may be particularly helpful for confused and/or aggressive and/or combative patients that may attempt to dislodge the tube. By maintaining the proper position of the tube within the patient, such as by maintaining distal tube end 103 at a proper distance within the patient's stomach may reduce risk of aspiration related to proximal migration of the tube or coiling in the esophagus. For example, the tube may be inserted into the patient, such as via a nostril, then the functional position of the tube (e.g., the distal tube end) inside the patient may be verified (e.g., via X-ray to ensure the distal tube end is in the stomach), and then the remainder of assembly 100 (e.g., subassemblies 110, 120, and 130, with or without liner 170) may be implemented with respect to that properly positioned tube for securely maintaining that proper tube position with respect to the patient's head.

As one example of use of assembly 100, once tube 102 has been properly positioned within the patient, such as through left nostril LN, an operator may attach one side of the straps of strap subassembly 110 to one side of mount subassembly 120, if they haven't been already, such as by looping lower right strap end 111 of lower right strap 112 through lower right opening 121l of mount base 124 and by looping upper right strap end 113 of upper right strap 114 through upper right opening 121u of mount base 124. Then, the operator may movably couple slider clamp 150 to slider clamp mount track body 126 of mount subassembly 120, if it isn't yet already. Then the operator may position mount base 124 underneath patient's nose PN, such as along and above the upper lip of patient's mount PM, and then the operator may slide slider lock subassembly 130 along mount subassembly 120 such that tube clamp 140 is underneath the nostril into which tube 102 is entering the patient. Tube clamp 140, with or without liner 170 therein, may be rotated up (e.g., in the direction of arrow CO about hinge 148h) with respect to slider clamp 150 and mount subassembly 120 in order to more easily press a portion of tube 102 into passageway 145 of tube clamp body 142 via opening 147 and into passageway 175 of tube liner body 172 via opening 177, if provided. Then, once tube 102 has been positioned to extend through tube clamp body 142 of slider lock subassembly 130, whether or not also through any tube liner 170, the operator may use (e.g., ratchet) tube adjuster 160 to contract tube clamp body 142 to clamp and hold tube 102 with respect to tube clamp body 142 (e.g., such that the portion of tube 102 extending within passageway 145 between bottom 149 and top 141 may not be pulled downwardly out from passageway 145 beyond bottom 149 and/or may not be pulled upwardly out from passageway 145 beyond top 141 and/or may not be pulled outwardly from passageway 145 through opening 147). The operator may tighten or loosen tie 162 with respect to pawl 168 in order to stabilize tube 102. The operator may pull on tube 102, such as the portion extending downwardly out from passageway 145 below bottom 149, to ensure that tube 102 does not slide with respect to tube clamp 140. Then, the operator may wrap a portion of strap subassembly 110 behind patient's head PH in order to loop end 115 of lower left strap 116 below left ear LE and through lower left opening 129*l* of mount base 124 and by looping end 117 of upper left strap 118 above left ear LE and through upper left opening 129*u* of mount base 124. Then, the operator may selectively adjust the length of one or more of straps 112, 114, 116, and 118 extending between strap base 110*b* and mount subassembly 120 (e.g., by varying the position at which a strap's free end is coupled to another portion of strap subassembly 110 after passing through an opening of mount subassembly 120), which may allow for tube holding assembly 100 to be securely yet comfortably worn on any suitably sized patient's head PH and such that mount base 124 may be securely yet comfortably held underneath patient's nose PN (e.g., above and along the upper lip of patient's mouth PM) while at least a portion of strap subassembly 110 (e.g., base 110*b*) may be held against a portion of the back of patient's head PH (e.g., while lower right strap 112 may extend between base 110*b* and mount base 124 underneath the patient's right ear RE, while upper right strap 114 may extend between base 110*b* and mount base 124 above the patient's right ear RE, while lower left strap 116 may extend between base 110*b* and mount base 124 underneath the patient's left ear LE, while upper left strap 118 may extend between base 110*b* and mount base 124 above the patient's left ear LE, and/or while top strap 119 may extend over the top of patient's head PH). The operator may ensure that the back of strap subassembly 110 (e.g., base 110*b*) is centered at the back of patient's head PH and, if not, may loosen or tighten any of the straps from either side to correct this. Alternatively, once tube 102 is properly positioned with respect to the patient (e.g., extending into a nostril) and once slider lock subassembly 130 has been coupled to mount subassembly 120, the operator may fully assemble strap subassembly 110 to mount subassembly 120 and attach strap subassembly 110 and mount subassembly 120 to patient's head PH (e.g., such that mount base 124 may extend along and above patient's mouth PM). Then, the operator may move (e.g., slide) slider lock subassembly 130 along mount subassembly 120 horizontally (e.g., in the direction of arrow SL or arrow SR) such that tube clamp 140 is properly aligned with tube 102 (e.g., underneath a nostril into which the tube extends) and/or may move (e.g., rotate) tube clamp 140 with respect to slider clamp 150 and mount subassembly 120 (e.g., about hinge 148*h* (e.g., in the direction of arrow CC or arrow CO)) such that tube clamp opening 147 of tube clamp body 142 is properly aligned with tube 102 for making easier the insertion of tube 102 through opening 147 into passageway 145. Then, tube 102 may be clamped and held within tube clamp body 142, and tube clamp 140 may be allowed to freely rotate about hinge 148*h* with respect to slider clamp 150 and mount subassembly 120 and freely slide with respect to mount subassembly 120 along track body 126 while tube 102 may remain properly positioned with respect to the patient despite such limited freedom of movement of tube clamp 140 with respect to mount subassembly 120. As shown, tube clamp passageway 145 may generally extend perpendicular to each one of arrows SL and SR when subassembly 130 is coupled to subassembly 120, no matter how body 142 may be positioned with respect to body 158 using hinge 148*h* (e.g., hinge 148*h* may enable body 142 to rotate with respect to body 158 about an axis of rotation that may be parallel to and/or linear with arrow SL and/or arrow SR (e.g., when body 158 is at a particular position along the track (e.g., even when the track may be curved)) and/or that may be perpendicular to an axis of passageway 145 along which body 142 may hold a portion of tube 102).

Figure 13A:
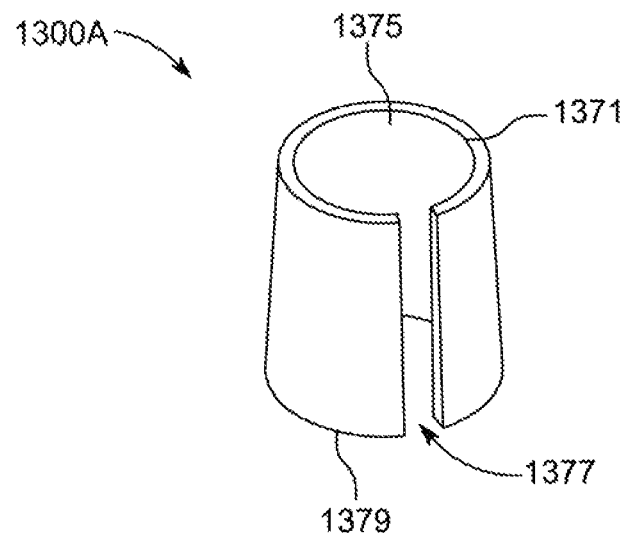
FIG. 13A is a front, top perspective view of a tube stopper in isolation.
Figure 13B:
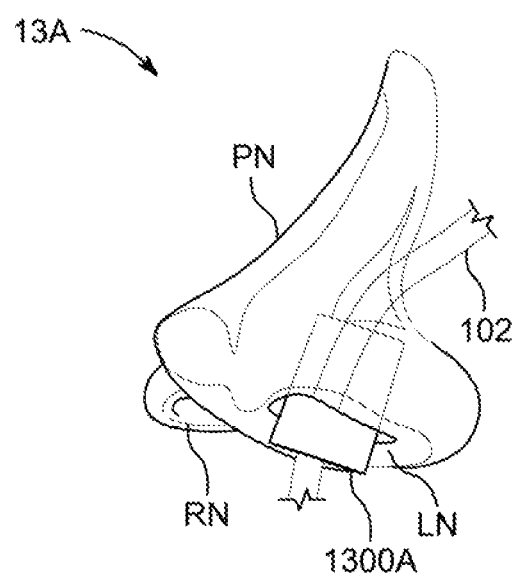
FIG. 13B is a front, top perspective view of the tube stopper of FIG. 13A and a tube positioned within a nostril of a patient.
Figure 13C:
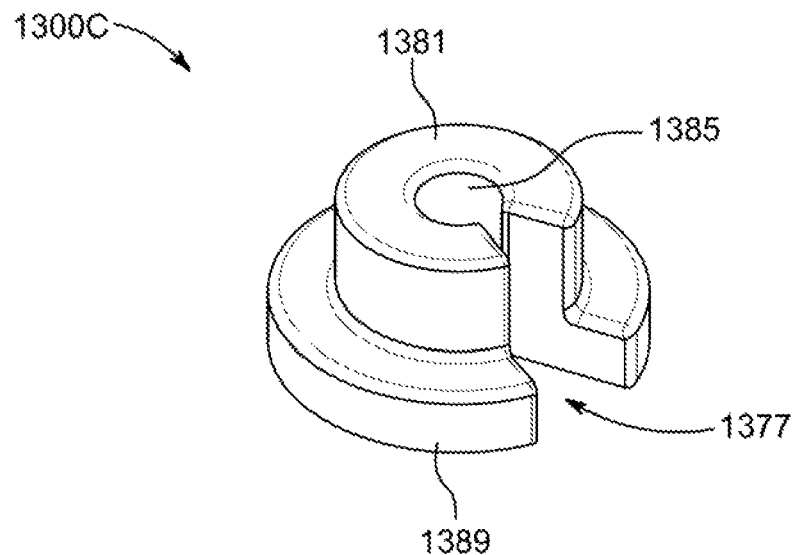
FIG. 13C is a front, top perspective view of another tube stopper in isolation.
Figure 13D:
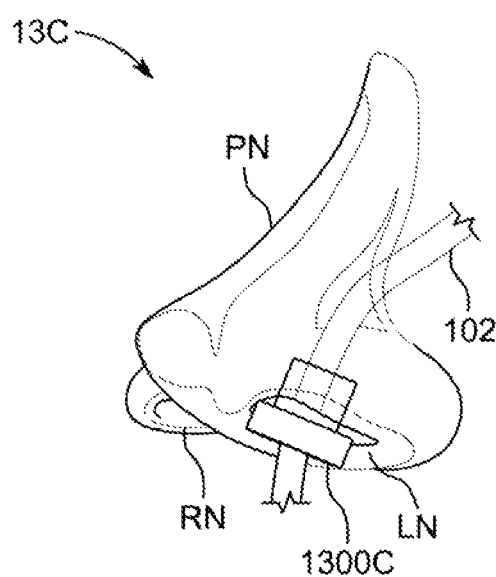
FIG. 13D is a front, top perspective view of the tube stopper of FIG. 13C and a tube positioned within a nostril of a patient.
Figure 13E:
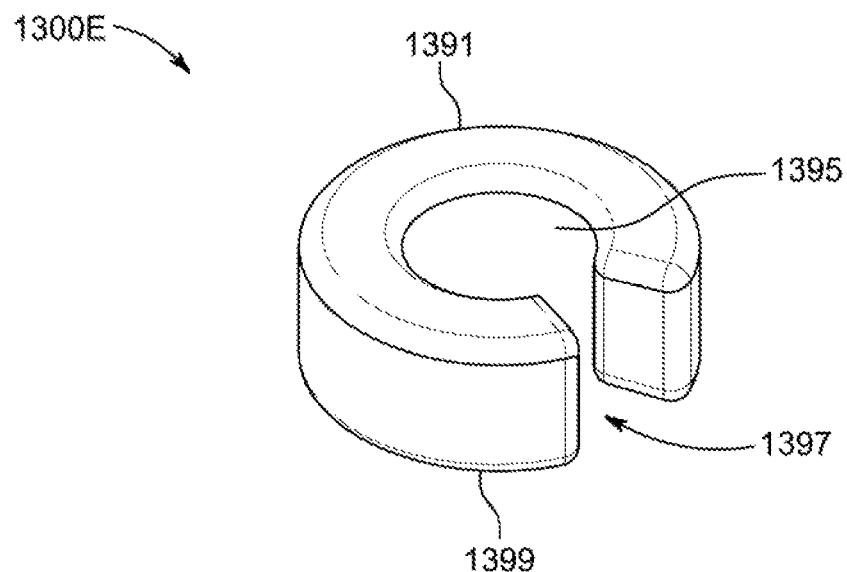
FIG. 13E is a front, top perspective view of yet another tube stopper in isolation.
Figure 13F:
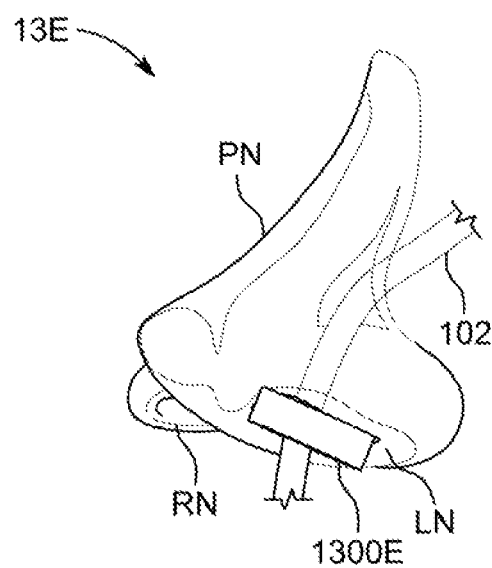
FIG. 13F is a front, top perspective view of the tube stopper of FIG. 13E and a tube positioned within a nostril of a patient.

In some embodiments, in addition to or as an alternative to any of the components of assembly 100, a tube stopper may be provided about a portion of a tube for helping to hold the portion of the tube within a nostril of a patient. For example, as shown in FIG. 13A, a tube stopper 1300A may be a hollow conical shaped stopper extending between a top end 1371 and a bottom end 1379 that may be larger than top end 1371 through which a passageway 1375 may extend and may be exposed by an opening 1377, similar to liner 170. This may enable a portion of tube 102 to be passed (e.g., pressed) through opening 1377 and into passageway 1375 and such that at least top end 1371 may then be inserted into nostril LN, which may center tube 102 within the nostril or otherwise remove tube 102 from rubbing against an inner surface of the nostril, as shown by system 13A of FIG. 13B. Stopper 1300A may be configured to easily fit into and/or grip any suitable nostril and/or to grip and prevent slippage of any tube extending therethrough. As another example, as shown in FIG. 13C. a tube stopper 1300C may be a hollow stepped ring stopper extending between a top cylindrical end 1381 and a bottom cylindrical end 1389 that may be larger than top cylindrical end 1381 through which a passageway 1385 may extend and may be exposed by an opening 1387. This may enable a portion of tube 102 to be passed (e.g., pressed) through opening 1387 and into passageway 1385 and such that at least top cylindrical end 1381 may then be inserted into nostril LN, which may center tube 102 within the nostril or otherwise remove tube 102 from rubbing against an inner surface of the nostril, as shown by system 13C of FIG. 13D. Top cylindrical end 1381 of stopper 1300C may be configured to easily fit into and/or grip any suitable nostril and/or to grip and prevent slippage of any tube extending therethrough, while stepped bottom cylindrical end 1389 may prevent stopper 1300C and tube 102 from being pulled further into the nostril and/or prevent stopper 1300C and tube 102 from getting dislocated sideways. As yet another example, as shown in FIG. 13E. a tube stopper 1300E may be a hollow flanged stopper extending between a top cylindrical end 1391 and a bottom cylindrical end 1399 through which a passageway 1395 may extend and may be exposed by an opening 1397. This may enable a portion of tube 102 to be passed (e.g., pressed) through opening 1397 and into passageway 1395 and such that at least top cylindrical end 1391 may then be inserted into nostril LN, which may center tube 102 within the nostril or otherwise remove tube 102 from rubbing against an inner surface of the nostril, as shown by system 13E of FIG. 13F.

Top cylindrical end 1391 of stopper 1300E may be configured to easily fit into and/or grip any suitable nostril and/or to grip and prevent slippage of any tube extending therethrough, while bottom cylindrical end 1399 may prevent stopper 1300E and tube 102 from being pulled further into the nostril.

Any suitable stopper may be coupled to or integrated with any suitable clip or clamp for more securely fixing the stopper to a tube and/or for enabling the stopper to be coupled to a mount subassembly of a strapped tube holding assembly. For example, as shown in FIGS. 14A-14C, the bottom end of stopper 1300A (e.g., bottom end 1379) may be coupled to (e.g., adhered to) or integrated with (e.g., molded (e.g., double shot molded) with) a top end of a locking mechanism or hinged clip 1400A that may include a first portion 1402 and a second portion 1408 rotatably coupled about a hinge portion 1405 for either exposing passageway 1375 of stopper 1300A and clip 1400A for enabling tube 102 to be positioned therein or for closing clip 1400A about tube 102. As shown, portion 1402 may include any suitable feature(s) 1402f and portion 1408 may include any suitable feature(s) 1408f, where such features may interact with one another to hold portions 1402 and 1408 together when portions 1402 and 1408 are rotated about hinge 1405 towards one another. Feature 1402f may interact and engage with a first portion of feature 1408 for clamping about a first tube 102' with a passageway of a cross-section (e.g., diameter) DP' (see, e.g., FIG. 14B), while feature 1402f may interact and engage with a second portion of feature 1408 for clamping about a second tube 102 with a passageway of a cross-section (e.g., diameter) DP (see, e.g., FIG. 14C) that may be smaller than DP', such that hinged clip 1400A with stopper 1300A may tightly hold different sized tubes. Alternatively, as shown in FIGS. 14D and 14E, the bottom end of stopper 1300A (e.g., bottom end 1379) may be coupled to (e.g., adhered to) or integrated with (e.g., molded (e.g., double shot molded) with) a top end of a locking mechanism or C-shaped clamp 1400D that may include a first portion 1402' and a second portion 1408' for either exposing passageway 1375 of stopper 1300A and clip 1400D for enabling tube 102 to be positioned therein or for closing clamp 1400D about tube 102. As shown, portion 1402' may include any suitable feature(s) 1402f and portion 1408' may include any suitable feature(s) 1408f, where such features may interact with one another to hold portions 1402' and 1408' together when portions 1402' and 1408' are squeezed together. While stopper 1300A may be made of any suitable soft material for comfortably interacting with the inside of intimate exterior of a nostril, each one of locking mechanism or clip 1400A and/or locking mechanism or clamp 1400D may be made of a more rigid material for more firmly grabbing or contracting around a tube for holding the tube in a particular position with respect to the stopper.

Figure 15A:
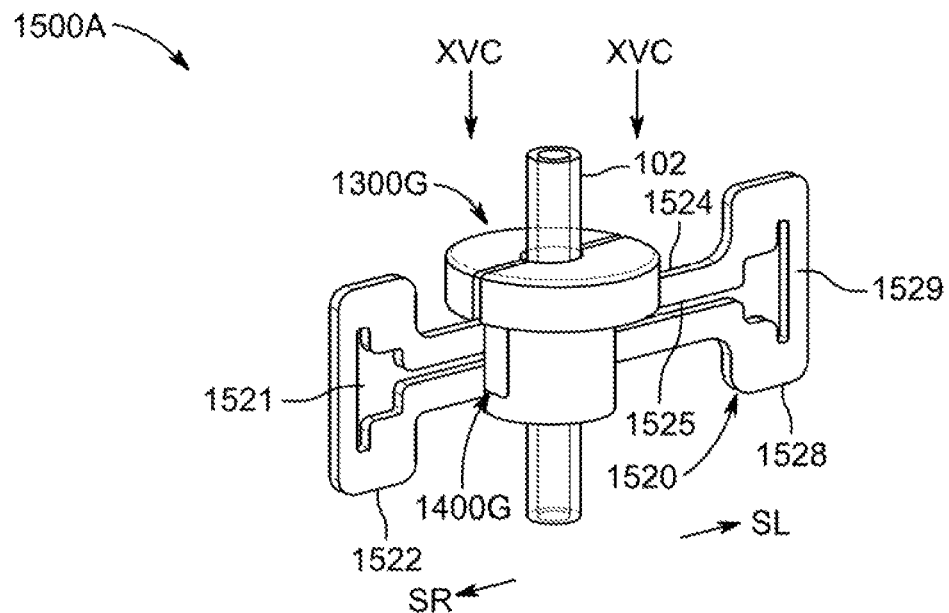
FIG. 15A is a front, right, top perspective view of yet another tube stopper with a locking mechanism about a tube and coupled to a mount of another tube holding assembly.
Figure 15B:
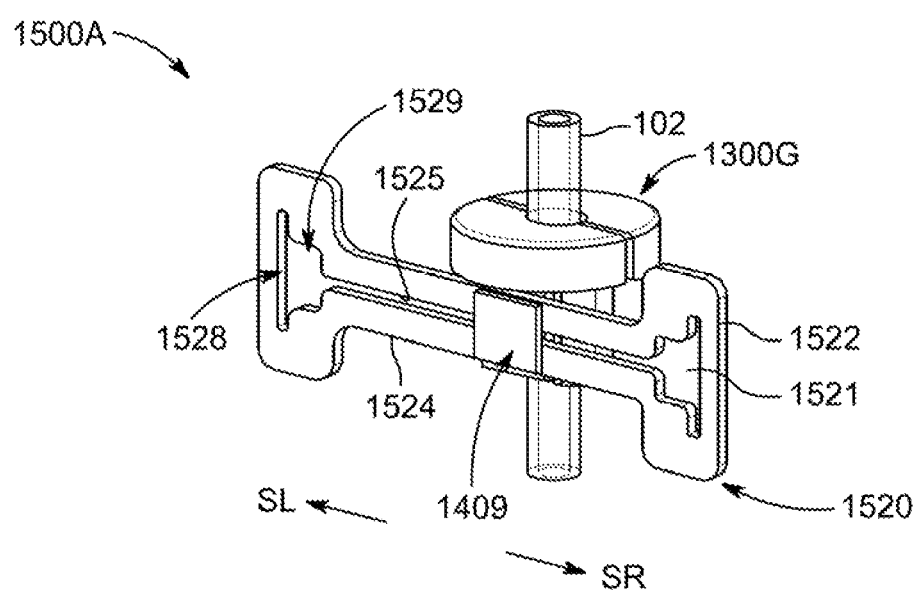
FIG. 15B is a rear, right, top perspective view of the tube holding assembly of FIG. 15A.
Figure 15C:
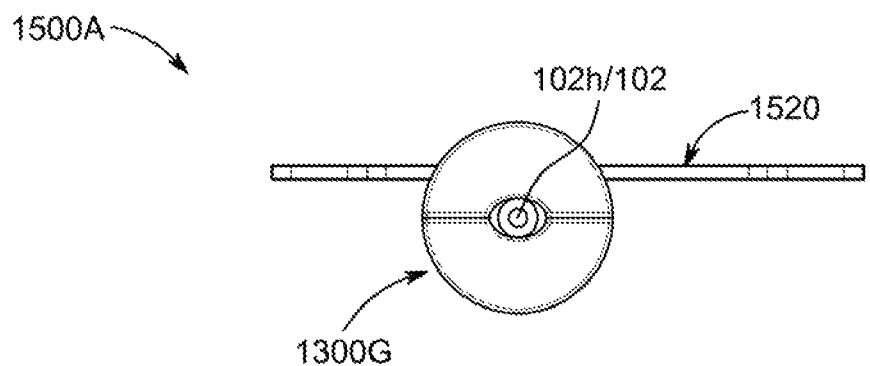
FIG. 15C is a top view of the tube holding assembly of FIGS. 15A and 15B, taken from line XVC-XVC of FIG. 15A.
Figure 15D:
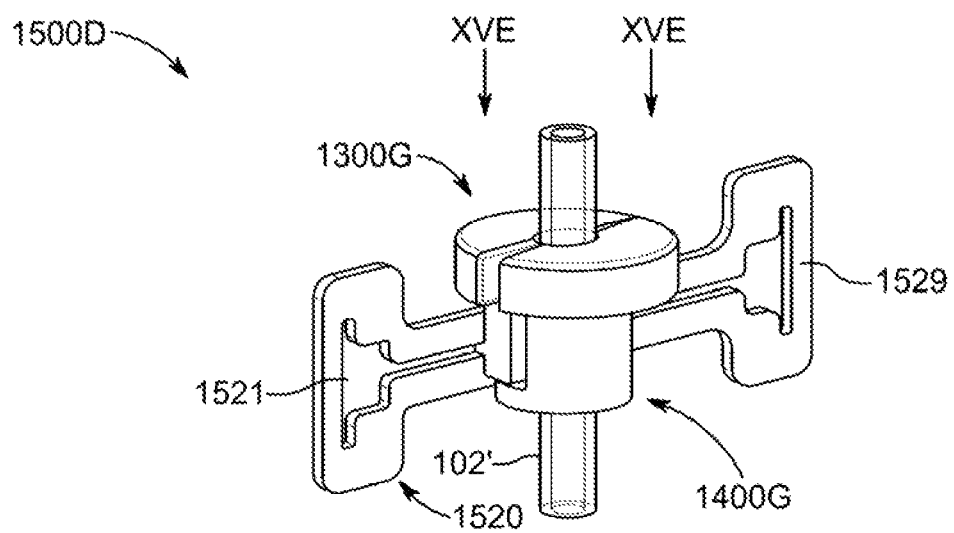
FIG. 15D is a front, right, top perspective view of yet another tube stopper with a locking mechanism about a tube and coupled to a mount of another tube holding assembly.
Figure 15E:
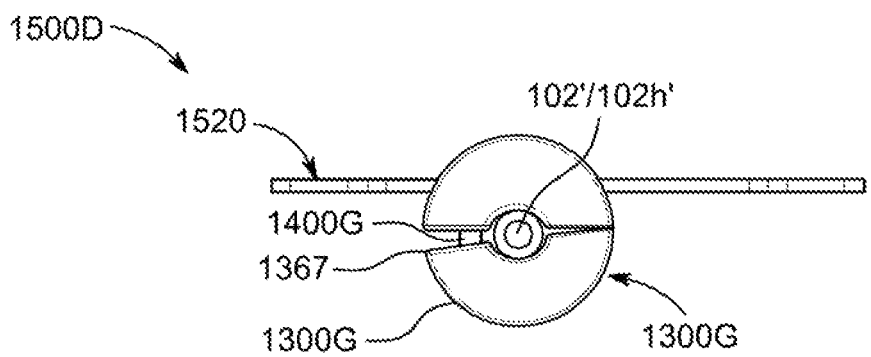
FIG. 15E is a top view of the tube holding assembly of FIG. 15D, taken from line XVE-XVE of FIG. 15D.

A combined stopper and locking mechanism may be slidably coupled to a mounting subassembly that may be strapped to a patient's head. For example, as shown in FIGS. 15A-15C, 16, 17A, and 17B, a tube holding assembly 1500A may include tube 102 held by a disc shaped stopper 1300G coupled to or integrated with a locking mechanism 1400G, while locking mechanism 1400G (e.g., an extender portion 1409) may be slidably coupled to a mounting subassembly 1520 that may include a mount body 1524 extending between a right end 1522 including an opening 1521 and a left end 1528 including an opening 1529 and a track space 1525 extending between openings 1521 and 1529. An end 1511 of a lower strap 1512 of a strap subassembly 1510 may be passed through opening 1521 and coupled to strap subassembly 1510 with any suitable fastening mechanism 1511f, an end 1513 of an upper strap 1514 of strap subassembly 1510 may be passed through opening 1521 and coupled to strap subassembly 1510 with any suitable fastening mechanism 1513f, another end of lower strap 1512 of strap subassembly 1510 may be passed through opening 1529 and coupled to strap subassembly 1510 with any suitable fastening mechanism, and another end of upper strap 1514 of strap subassembly 1510 may be passed through opening 1529 and coupled to strap subassembly 1510 with any suitable fastening mechanism. A base 1510b of strap subassembly 1510 may extend between a portion of upper strap 1514 and a portion of lower strap 1512 for providing support to a rear portion of patient's head PH when strap subassembly 1510 and mounting subassembly 1520 are coupled to each other and strapped to patient's head PH. A protective flap 1580 may be provided underneath at least a portion of strap subassembly 1510 such that a top portion 1582 of flap 1580 may be folded down over end 1513 and fastening mechanism 1513f (e.g., from the configuration of FIG. 17A to the configuration of FIG. 17B) to prevent the patient from being able to access fastening mechanism 1513f for removing assembly 1500A from patient's head PH and/or such that a bottom portion 1588 of flap 1580 may be folded up over end 1511 and fastening mechanism 1511f (e.g., from the configuration of FIG. 17A to the configuration of FIG. 17B) to prevent the patient from being able to access fastening mechanism 1511f for removing assembly 1500A from patient's head PH. Additionally or alternatively, another flap or the same flap may be provided for covering other fastening mechanisms (e.g., on the other side of the head). Extender portion 1409 of locking mechanism 1400G may be sized and/or shaped to pass through one of openings 1521 and 1529 for accessing track space 1525 along which extender portion 1409 may slide locking mechanism 1400G and thus tube 102 with respect to mounting subassembly 1520 (e.g., in the direction of arrow SL or arrow SR). Disc shaped stopper 1300G may include an opening 1367 that may enable larger tubes (e.g., tube 102') to be positioned within the passageway of the stopper and locking mechanism (see, e.g., assembly 1500D of FIGS. 15D and 15E). One or more loops 1599 (e.g., hook and fastener equipped ties) may be provided to loop around a strap of subassembly 1510 and a portion of tube 102 for holding tube 102 against strap subassembly 1510 rather than enabling tube 102 to be loose and potentially snag on an ambient element or be grabbed easily by the patient.

While there have been described tube holding assemblies and methods for using and making the same, it is to be understood that many changes may be made therein without departing from the spirit and scope of the subject matter described herein in any way. Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements. It is also to be understood that various directional and orientational terms, such as "proximal" and "distal," "up" and "down," "front" and "back," "top" and "bottom" and "side," "length" and "width" and "thickness" and "diameter" and "cross-section" and "longitudinal," "X-" and "Y-" and "Z-," and the like, may be used herein only for convenience, and that no fixed or absolute directional or orientational limitations are intended by the use of these words. For example, the assemblies and patients can have any desired orientations. If reoriented, different directional or orientational terms may need to be used in their description, but that will not alter their fundamental nature as within the scope and spirit of the subject matter described herein in any way.

Therefore, those skilled in the art will appreciate that the invention can be practiced by other than the described embodiments, which are presented for purposes of illustration rather than of limitation.

What is claimed is:

1. A method of using an assembly for holding a nasogastric tube to a patient's head once a distal end of the nasogastric tube has been functionally positioned within the patient via a nostril of a nose of the patient, the method comprising:
    positioning a mount subassembly of the assembly underneath the nose such that a track of the positioned mount subassembly extends above and along an upper lip of the patient;
    sliding a slider clamp body of a lock subassembly of the assembly along the track of the positioned mount subassembly until a tube clamp body of the lock subassembly is aligned with a portion of the nasogastric tube;
    rotating the tube clamp body with respect to the slid slider clamp body until a passageway of the tube clamp body is aligned with the portion of the nasogastric tube; and
    placing the portion of the nasogastric tube within the passageway of the rotated tube clamp body.

2. The method of claim 1, wherein the placing comprises pressing the portion of the nasogastric tube towards the track and into the passageway.

3. An assembly for holding a nasogastric tube to a patient's head, the assembly comprising:
    a mount subassembly comprising:
        a base; and
        a track extending from and along a front face of the base;
    a lock subassembly comprising:
        a slider clamp body operative to be coupled to and slidable along the track;
        a tube clamp body; and
        a hinge operative to allow movement of the slider clamp body with respect to the tube clamp body; and
    a strap subassembly operative to secure the mount subassembly to the patient's head, wherein:
        the tube clamp body defines a tube clamp passageway along a length of an interior of the tube clamp body extending between a tube clamp body top and a tube clamp body bottom;
        the tube clamp body is operative to hold a portion of the nasogastric tube in place with respect to the tube clamp body within the tube clamp passageway and along the length of the interior of the tube clamp body;
        the tube clamp passageway is accessible by the portion of the nasogastric tube via a tube clamp body opening extending through a front face of the tube clamp body and between the tube clamp body top and the tube clamp body bottom;
        the tube clamp body opening is operative to introduce the portion of the nasogastric tube into the tube clamp passageway; and
        when the slider clamp body is coupled to the track, the hinge is operative to allow movement of the slider clamp body with respect to the tube clamp body such that the tube clamp passageway is positioned between the tube clamp body opening and the track.

4. The assembly of claim 3, wherein the hinge is a living hinge coupling the slider clamp body to the tube clamp body.

5. The assembly of claim 3, wherein the lock subassembly further comprises an adjuster operative to adjust a cross-sectional area of the tube clamp passageway.

6. The assembly of claim 5, wherein the adjuster comprises an adjuster tie and a pawl.

7. The assembly of claim 3, further comprising a tube liner body positioned within the tube clamp passageway.

8. The assembly of claim 7, wherein the tube liner body defines a tube liner passageway along and within which the tube liner body is operative to hold the portion of the nasogastric tube in place with respect to the tube clamp body.

9. The assembly of claim 3, wherein the hinge is operative to allow movement of the slider clamp body with respect to the tube clamp body such that the tube clamp body opening faces away from the slider clamp body when the slider clamp body is coupled to the track.

10. The assembly of claim 9, wherein:
    the hinge is operative to allow rotation of the slider clamp body with respect to the tube clamp body about an axis of rotation; and
    the axis of rotation is parallel to a direction of the track along which the slider clamp body is slidable when the slider clamp body is coupled to the track.

11. The assembly of claim 10, wherein the track is at least partially curved.

12. The assembly of claim 3, wherein the hinge is operative to allow rotation of the slider clamp body with respect to the tube clamp body about an axis of rotation.

13. The assembly of claim 12, wherein the axis of rotation is parallel to a direction of the track along which the slider clamp body is slidable when the slider clamp body is coupled to the track.

14. The assembly of claim 13, wherein the track is at least partially curved.

15. The assembly of claim 3, wherein the track is at least partially curved.

16. The assembly of claim 3, wherein:
    a track space is defined by the base and the track;
    the track space extends between a first track end and a second track end;
    a feature of the slider clamp body is operative to be held within the track space; and
    the slider clamp body is free to slide along the track between the first track end and the second track end when the feature of the slider clamp body is held within the track space.

17. The assembly of claim 3, wherein:
    the base comprises a strap opening;
    the strap subassembly comprises a strap extending between a first strap end and a second strap end;
    the first strap end is coupled to the base; and
    the second strap end is operative to be fed through the strap opening for adjusting a length of the strap operative to extend about a portion of the patient's head for securing the mount subassembly to the patient's head.

18. The assembly of claim 17, wherein the strap subassembly further comprises:
    a strap end fastening mechanism operative to fix the length of the strap; and
    a flap operative to cover the strap end fastening mechanism for hiding the strap fastening mechanism from the patient.

19. The assembly of claim 3, wherein an axis of rotation is above the track along which the slider clamp body is slidable when the slider clamp body is coupled to the track.

20. An assembly for holding a nasogastric tube to a patient's head, the assembly comprising:
- a mount subassembly defining a track;
- a lock subassembly comprising:
  - a slider clamp body operative to be coupled to and slidable along the track;
  - a tube clamp body operative to receive and hold a portion of the nasogastric tube in place with respect to the tube clamp body; and
  - a hinge operative to allow rotation of the slider clamp body with respect to the tube clamp body about an axis of rotation; and
- a fastener subassembly operative to secure the mount subassembly to the patient's head such that the axis of rotation is positioned between the patient's nose and mouth and such that the axis of rotation is positioned between the patient's nose and the track when the slider clamp body is coupled to the track.

* * * * *